US008852312B2

(12) United States Patent
Chandratre

(10) Patent No.: US 8,852,312 B2
(45) Date of Patent: Oct. 7, 2014

(54) SYSTEM AND METHOD FOR BIOLOGICAL TREATMENT OF BIODEGRADABLE WASTE INCLUDING BIODEGRADABLE MUNICIPAL SOLID WASTE

(76) Inventor: Maithilee Dinesh Chandratre, Maharashtra (IN)

( * ) Notice: Subject to any disclaimer, the term of this patent is extended or adjusted under 35 U.S.C. 154(b) by 301 days.

(21) Appl. No.: 13/382,128
(22) PCT Filed: Dec. 29, 2009
(86) PCT No.: PCT/IN2009/000743
§ 371 (c)(1), (2), (4) Date: Feb. 3, 2012
(87) PCT Pub. No.: WO2011/036675
PCT Pub. Date: Mar. 31, 2011

(65) Prior Publication Data
US 2012/0131969 A1 May 31, 2012

(30) Foreign Application Priority Data
Sep. 22, 2009 (IN) .......................... 2187/MUM/2009

(51) Int. Cl.
C05F 11/08 (2006.01)
B09B 3/00 (2006.01)
C05F 17/00 (2006.01)
C12M 1/34 (2006.01)
C12M 1/107 (2006.01)
C02F 11/04 (2006.01)
C05F 9/00 (2006.01)
C12M 1/00 (2006.01)
C12M 1/26 (2006.01)
C12M 1/10 (2006.01)

(52) U.S. Cl.
CPC ............... B09B 3/00 (2013.01); C05F 17/0027 (2013.01); C12M 41/12 (2013.01); C02F 2209/06 (2013.01); C12M 21/04 (2013.01); C02F 11/04 (2013.01); C12M 23/36 (2013.01); C02F 2209/02 (2013.01); C12M 41/26 (2013.01); C05F 9/00 (2013.01); C12M 27/20 (2013.01); C12M 45/04 (2013.01); C12M 33/20 (2013.01); Y02E 50/343 (2013.01)
USPC .......................... 71/10; 435/262.5; 435/290.4

(58) Field of Classification Search
USPC .................... 209/38; 71/10; 435/290.4, 262.5
See application file for complete search history.

(56) References Cited

U.S. PATENT DOCUMENTS 4,264,352 A * 4/1981 Houser ............................... 71/9
4,356,269 A * 10/1982 Thomsen et al. ........... 435/290.2
(Continued)

FOREIGN PATENT DOCUMENTS

DE 34 20 433 12/1985
DE 3420433 * 12/1985
(Continued)

OTHER PUBLICATIONS

International Search Report for International Application No. PCT/IN2009/000743 dated Oct. 11, 2011.

Primary Examiner — Wayne Langel
(74) Attorney, Agent, or Firm — Wiley Rein LLP

(57) ABSTRACT

The present invention relates to a Method and system for completion of Ecological cycle of Biomass, applying Nature to Nature (N2N) theory, by biological treatment of any biodegradable waste or organic waste, including biodegradable part of MSW, to produce rich biological fertilizer as end product, methane and many useful byproducts using natural processes and natural/organic materials within a very short time span. Thus, whatever is taken from nature is returned back to the nature in natural time span called as N2N Theory.

12 Claims, 7 Drawing Sheets

(56) References Cited

U.S. PATENT DOCUMENTS

| | | | | |
|---|---|---|---|---|
| 5,591,637 | A | * | 1/1997 | Inoue .................... 435/290.2 |
| 6,071,740 | A | * | 6/2000 | Kerouac ................. 435/290.3 |
| 6,887,692 | B2 | * | 5/2005 | Paterek .................... 435/168 |
| 7,410,583 | B2 | * | 8/2008 | Gray et al. ................ 210/603 |
| 8,124,401 | B2 | * | 2/2012 | Dutil et al. .............. 435/262.5 |
| 2005/0260744 | A1 | * | 11/2005 | Campbell ............... 435/290.2 |
| 2009/0095673 | A1 | | 4/2009 | Choate et al. |
| 2009/0209025 | A1 | * | 8/2009 | Goschl et al. ............ 435/262.5 |
| 2013/0291608 | A1 | * | 11/2013 | Johnson ........................ 71/10 |

FOREIGN PATENT DOCUMENTS

| | | | |
|---|---|---|---|
| DE | 195 08 785 | | 9/1995 |
| DE | 197 19 895 | | 11/1998 |
| DE | 197 19 895 C 1 | * | 11/1998 |
| FR | 2 924 038 | | 5/2009 |

* cited by examiner

SYSTEM AND METHOD FOR BIOLOGICAL TREATMENT OF BIODEGRADABLE WASTE INCLUDING BIODEGRADABLE MUNICIPAL SOLID WASTE

CROSS-REFERENCE TO RELATED APPLICATIONS

This application is a National Stage of International Patent Application PCT/IN2009/000743, filed Dec. 29, 2009, which claims priority to foreign Indian Patent Application No. 2187/MUM/2009, filed Sep. 22, 2009, the disclosures of which are incorporated by reference in their entireties.

FIELD OF THE INVENTION

The present invention relates to treatment of biodegradable waste including biodegradable municipal solid waste for producing products, such as rich biological/organic fertilizers, methane, and many useful byproducts the like, in short time span.

PRIOR ART

There are varieties of methods which are currently used for disposing the waste on the basis of their operating systems, the methods are as follows:
I. Biodegradation.
II. Incineration
III. Mechanical Biological Treatment plant—MBT Bio Degradation: This method has been commonly used since many centuries where the waste is disposed off and is allowed to bio degrade naturally. On the basis of the available area of land, manpower and resources the following procedures are followed:

A. Open Landfills: This method is commonly followed in many cities in India and all over the world. In this system the collected waste which is a mixed waste is dumped in the landfill, without any prior processing Disadvantages of this are
1. Natural biodegradation takes a very long time of monts or even years
2. Because of the mixed nature of the waste various un-natural chemical reactions take place & there is formation of lechate which percolates into the soil, contaminating the soil layers & also the natural ground water table to a great extent. Thus Fertility of the soil in the adjoining areas is lost gradually, for its lifetime
3. Potent green house gases like methane, CO2 & some Hazardous gases are generated and liberated from the landfill causing air pollution
4. Openly kept waste invites flies, mosquitoes etc. and thus various diseases
5. Landfills usually catch fire in the summers & which is difficult to control, even for months, causing extensive air pollution. Also landfill are main contributors for global warming.
6. Area which is used for these open landfills is a waste of land area, which will be of no use for any other purpose for at least the next 80 to 100 years.

B. Closed Landfills:
This system is parallel to the open landfill system, the only difference being the mixed MSW coming daily is spread on the landfill site and it is covered by a layer of soil and the material is allowed to decompose in the natural way, but disadvantage of the open landfill remains the same.

C. Composting
Tunnel composting, vessel composting: These processes are similar to the landfills because they allow the MSW to degrade naturally.
Vermi composting, which is a type of composting where earthworms are used for natural decomposition.
However, these processes have the disadvantages that they cannot be done in very large quantities as in cities II Incineration
The basic principle in the incineration process is the burning of the MSW in closed RCC chambers under controlled temperature and depending upon the temperature incineration process is classified into following methods:
A. Pyrolysis
B. Plasma gasification
C. Incineration A. Pyrolysis:
This pyrolysis is burning of hazardous materials in a closed chamber at approximately 300° C. and converting all such material to ash which does not carry any biological value.

B. Plasma Gasification or Incineration
In this system an arc of fire is formed in a closed, heavy capacity RCC chamber and the temperature is raised to 600 c to 3000 c, even 13000 to 15000 c depending upon the material to be treated
In this chamber mixed waste burns to produce gases or fly ash as a by product III Mechanical Biological Treatment Plant
In this process all different combinations of either single or many methods mentioned above are used, on with complicated mechanical process ultimately to produce refused derived fuel (RDF) or electricity.

DISADVANTAGES OF THE PRIOR ART

The plasma gasification/incineration chamber has to be made of heavy duty concrete and in large volumes and thus the initial cost of installation is very high. similarly initial & running costs of MBT's is also very high This particular process creates heavy amount of inert material i.e. fly ash and will create a major problem in the near future and it does not carry any biological value.

OBJECT OF THE INVENTION

Object of present invention is to provide method and system for biological treatment of biodegradable waste (herein after referred as BW) including biodegradable municipal solid waste (herein after referred as MSW), which completes the 'Ecological Cycle of Biomass' by treating the biodegradable waste & thus to help to complete the Recycling II of Biomass & to make nutrients available for Recycling III & I Another object of the present invention is to provide a method and a system for treating BW including MSW to produce rich biological or organic fertilizers, methane and to produce useful intermediate products, by products & to install sub plants for various purposes.

Yet another object of the present invention is to provide a method and a system for treating BW including MSW, which is capable of reducing the time span to greater extent, as compared to the known/existing processes.

One more another object of the invention is to provide a method and a system for treating BW including MSW, which will produce products in natural form for completing the ecological and biological cycle of biomass in nature.

Further object of the present invention is to provide a method and a system for treating BW including MSW, which is easily erected at various locations & in various capacities and even a single capacity unit can also, be in multiple stages and at various locations.

Further one object of the present invention is to provide a method and a system for treating BW including MSW which will produce useful intermediate products, byproducts & sub plants which can be used for different purposes & in different industries.

Yet another object of invention is to provide the recycling plant for BW including MSW fulfilling most of the following criteria's:

The plant must be completing the perfect bio-geochemical cycle of all the fundamental elements and ultimately the bio-mass cycle or the food chain of the Universe.

Giving complete and natural solution.

The end product should be natural and useful ecologically

It must satisfy the criteria of closed chamber so that emitted green house gases can be collected and can be treated as per the environmental requirement. Thus, the % of global warming caused by them can be reduced.

It should be without leachate formation, to save the soil & water.

It must be affordable to implement at the grass root level.

It should have simple technology for erection/operation/maintenance at the grass root level.

It should be with minimum initial/operation/maintenance cost for the local governance.

It should be modular in nature, i.e., suitable to install in various modules/stages at various locations suitable to local governance.

SUMMARY OF INVENTION

The present invention describes a method and system which is developed for completion of Ecological cycle of Biomass, applying Nature to Nature theory (N2N Theory), by biological treatment of any biodegradable waste (herein after referred as BW) or organic waste, including biodegradable part of Municipal waste, to produce rich biological end product i.e. biological fertilizer, methane and many useful byproducts For which a 'Biological Treatment Plant' (BTP), will be called as BTP herein onwards is invented, which uses all natural methods based on natural processes, in series and modules, using natural materials, to treat any biodegradable waste (BW), to produce natural and biological end product along with methane and many useful byproducts. This will take place within a very short span of time, thus returning nature what is taken up from it within natural time span, so that nature will be able to maintain the 'Ecological Cycle of Biomass', and the theory can be called as Nature to Nature (N2N) theory of completion of ecological cycle of biomass.

This Biological treatment Plant is designed for the $21^{st}$ century for the treatment of BW.

'Biomass' means organic matter which is present in the body of every living organism, plants, & animals present in the nature. The carbohydrates, proteins and lipids are produced by plants as the basic food and this food mass is called as bio-mass. (called as 'Biomass' hereinafter, its cycle is called 'Ecological cycle of Biomass' hereinafter and Nature to nature theory applicable to biomass is called 'N2N Theory of Biomass', hereinafter). N2N theory means what ever is taken from the nature should be returned to the nature, which also applies to biomass.

Ecological Cycle Of Bio-Mass

To complete ecological cycle of bio-mass by N2N theory the bio-mass or the fundamental elements have to pass through 3 stages or media's i.e., Cycle gets completed in 3 stages (ref. FIG. 1)

Recycling Stage I—Nature to Plant Media to Animal Media

Plants prepare the basic food in the form of carbohydrates using the fundamental elements by carbon fixation by photosynthesis. Herbivores eat plants, carnivores eat herbivores, and omnivores eat both for their body metabolism.

Recycling Stage II—Animal Media to Soil Media

Animal digest what they eat and after their complete digestion process they produce excreta as a waste, called as sewage, which is normally composted in the soil.

Recycling Stage III—Soil Media to Soil Bacteria to Plant Media

When this excreta is mixed in the soil which is the basic food of the soil bacteria. The soil bacteria decompose the organic matter & produce basic nutrients. These nutrients are in the form of fundamental elements and are easily absorbed by the plants.

Plants absorb the basic elements from the soil as main nutrition and with the help of $CO_2$ from the atmosphere, $H2O$ from soil media and light energy from the sunlight, they undergo photosynthesis i.e carbon fixation and prepare the basic form of carbohydrates which is the generation of biomass, thus the cycle continues.

In the cycle of Biomass the plants are Producers, Animals are consumers & soil bacteria are Decomposers. Producers get the basic materials from Nature to produce the first form of food, Consumers use this food for their metabolism by digestion, Decomposers biodegrade all the waste organic matter & return it to Nature. Thus the Ecological cycle of Biomass is completed.

Thus ultimately through the Biomass cycle the basic elements are moving from the nature, through different media, in the Nature i.e they complete their bio-geo chemical cycles.

Thus after all these 3 stages of re-cycling of biomass, the bio-mass cycle is complete. In this BTP by treating the biodegradable waste, the Recycling Stage II i.e. that is animal media to soil media of biomass is completed, & good nutrients & elements are made available for the Recycling Stage III & I, which if not complete will break the chain of biomass of nature.

The biomass which does not pass through digestive system of any animal is treated in Biological Treatment Plant (BTP).

In general the entire waste created in nature is entirely bio-degradable material and it bio-degrades in the natural way, within natural time frame, which is acceptable to nature. Since in nature there is no excess waste, there is no need of a waste treatment process or plant for natural waste.

But in Humans—

The Biodegradable solid waste can be broadly categorized into 2 parts a. Sewage—The main sources of sewage are domestic and other toilets.

b. Solid—Normally known as Municipal Solid Waste i.e. (MSW)

Out of the existing processes Biodegradation is the only system which completes the biological/ecological chain or cycle however the time duration required is much more (i.e., from 30 days upto some months or even years). Considering the volumes of MSW in the 21st century, the requirement of land for the land fill, the amount of emission of green house and some hazardous gases, global warming due to green house gases, amount of leachate formation because of mixed nature of solid waste, and thus contaminating soil and ground water shall become unavoidable.

The management of MSW is mainly focused worldwide & has been given prime importance for treatment, but BW (Biodegradable waste) has not given independent importance.

The main object of invention is to give the prime focus on the treatment of any BW including MSW in the BTP. Rate of production of biodegradable solid waste is very fast. If it remains untreated it will lead to many environmental problems, which are very harmful to society & ultimately to the ecology.

All other types of wastes like inert, and non-biodegradable are recycled, but biodegradable wastes needs recycling with natural speed, which is possible in BTP as on today.

In this BTP all the biological reactions take place in series, as they take place in the digestive systems of animals and in nature (anaerobic digestion), with the end products such as enriched biological (organic) fertilizer, CH4 (methane), CO2 (carbon dioxide), H2O, Ammonia (NH3).

These end products when mixed in the soil are easily available for Recycling Stage III, and will reduce the processing time required for soil bacteria to biodegrade organic matter & thus will be made available to Recycling I fastly & gases are either used, or treated & mixed in the atmosphere, so that they can be used further by the nature.

All the animals including humans complete their entire digestion process approximately in 24-36 hours. There is no existing system or existing process available (except the digestive systems of humans and animals) till date for complete treatment of biodegradable material, in such a short time span, as it exists in the N2N theory, but, this is possible in the BTP.

The Comparison Chart

Thus, the digestive system of any living animal is based on the exact principle of N2N theory and the same is the case of BTP Thus the biomass in nature/food in the digestive systems of animals & BW in BTP both are treated in a similar way. Both are treated like Recycling Stage II. Both of these further have to enter into Recycling Stages III & I of nature to complete the cycle. Thus BTP helps to complete the biomass Cycle, as shown in FIG. 2.

STATEMENT OF THE INVENTION

According to the present invention there is provided a system for biological treatment of biodegradable waste, the system comprising;
- an unloading platform for unloading mixed solid waste having biodegradable waste and other wastes collected from various sources;
- at least one conveyor belt for conveying the mixed solid waste from the unloading platform;
- a magnet chamber provided next to the unloading platform, wherein the conveyor belt with the mixed solid waste is passed though the magnet chamber for separating metal part from the mixed solid waste;
- at least one separator provided next to the magnet chamber, wherein the recyclable inorganic waste is separated from mixed solid waste from the conveyor belt;
- a first storage tank provided next to the at least one separator, the first storage tanks enables segregation of the mixed solid waste;
- a primary treatment tank receives the segregated biodegradable waste from the first storage tank; the primary treatment tanks comprises;
    - a chamber for collecting the segregated biodegradable waste and mixing with hot water having temperature in the range of 70° C. to 140° C. to kill pathogens; and
    - a rotor for rotating/churning the segregated biodegradable waste mixed with hot water, wherein, upon rotating the mixture and allowing natural settling, the similar process is repeated at least twice, the biodegradable waste is separated from other non-biodegradable waste and supernatant water containing oil grease small particles, plastic and like, the water is further purified;
- a second storage tank disposed adjacent to the primary treatment tank, the sludge is further dehydrated and compacted therein, thereby reducing 80% to 50% of volume of the sludge, the second storage tank also includes a grinding mechanism, and a chopping mechanism of biodegradable waste to reduce the size of biodegradable waste, thereby increasing surface area which enhances the efficiency of the further treatment to form prepared sludge;
- a third storage tank disposed juxtaposition to the second storage tank, the third storage tank capable of collecting and storing the prepared sludge received from the second storage tank at a temperature ranging between 40° C. to 60° C.;
- at least one Biological Treatment Plant-I receives pumped prepared sludge from the third storage tank by means of a pump and strict anaerobic condition, temperature between 35° C. to 40° C., and controlled PH is maintained therein, wherein the prepared sludge is treated for predefined hours with a fluid i.e. ruminal fluid from the rumen of the cow or a 'Fluid' similar to it, with specific 'Microbes' to form treated slurry;
- at least one Biological Treatment Plant-II disposed juxtaposition to the Biological Treatment Plant-I and anaerobic condition, temperature between 35° C. to 40° C., and controlled PH is maintained therein, the Biological Treatment Plant-II receives treated slurry from the Biological Treatment Plant-I, and treated for predefined hours with enzymes' of or similar to human digestive systems i.e., pancreatic & intestinal enzymes & bile salts therein; and
- a Biological Treatment Plant-III disposed juxtaposition of the Biological Treatment Plant-II and anaerobic condition, temperature between 35° C. to 40° C., and controlled PH is maintained therein, the Biological Treatment Plant-III capable of maintaining anaerobic conditions for treating the received slurry from Biological Treatment Plant-II with thermophilic bacteria therein for predefined hours;
- wherein, upon treating the prepared sludge in Biological Treatment Plant-I, Biological Treatment Plant-II and Biological Treatment Plant-III, the biodegradable waste is converted into fertilizer and methane gas is librated from Biological Treatment Plant-I and Biological Treatment Plant-III, which is collected in a gas collector, whole process in BTP is biologically and mechanically enhanced to complete the treatment within approximately 48 to 72 hrs.

Typically, wherein the Biological Treatment Plant-I includes plurality of baffle walls and plurality of sprinklers, wherein the baffle wall enables enhanced movement of sludge therein, and the sprinklers enables mixing of the sludge with fluid i.e. ruminal fluid from the rumen of the cow or a 'Fluid' similar to it, with specific 'Microbes'.

Typically, wherein a pusher and a rotor is provided in Biological Treatment Plant I, Biological Treatment Plant II, and Biological Treatment Plant III, the pusher introduces waves in forward direction and the rotor to enhances proper mixing of ruminal fluid or enzymes in the prepared slurry.

Typically, wherein the Biological Treatment Plant-II includes plurality of baffle walls and plurality of sprinklers, wherein the baffle wall enables enhanced movement of slurry therein, and the sprinklers enables mixing of the slurry with Enzymes' of or similar to human digestive systems i.e., pancreatic & intestinal enzymes & bile salts.

Typically, wherein the Biological Treatment Plant-III includes plurality of baffle walls and plurality of sprinklers, wherein the baffle wall enables enhanced movement of slurry therein, and the sprinklers enables mixing of the thermophilic bacteria.

Typically, wherein the Biological Treatment Plant-I and Biological Treatment Plant-II are connected by at least one connecting element to pass the slurry from Biological Treatment Plant-I to Biological Treatment Plant-II, therebetween treated with acid to kill the microbes from Biological Treatment Plant-I.

Typically, wherein the Biological Treatment Plant-I, Biological Treatment Plant-II and Biological Treatment Plant-III having anaerobic condition, temperature between 35° C. to 40° C., and controlled PH is maintained therein.

According to the present invention there is also provided a method for biological treatment of biodegradable waste, the method comprising steps;
  loading the mixed solid waste on the conveyor belt;
  passing the conveyor belt containing mixed solid waste through a magnet chamber for separating metal parts from the mixed solid waste;
  further, passing the conveyor belt containing mixed solid waste through at least one separator; wherein the biodegradable waste is separated from the recyclable inorganic waste of mixed solid waste;
  thereafter, collecting the segregated biodegradable waste in a first storage tank;
  passing the segregated biodegradable waste from the first storage tank to primary treatment tank;
  further, treating the biodegradable waste in primary treatment tank; wherein the biodegradable waste mixed with hot water having temperature ranging between 70° C. to 140° C. to kill pathogens and simultaneously rotated with a rotor and allowing natural settling for predefined hours and the process is repeated at least twice for separation of non-degradable material and supernatent water containing oil, grease, and the like, to form prepared sludge, the separated supernatent water is purified in a water treatment plant;
  thereafter, dehydration and compaction of prepared sludge;
  thereafter grinding and chopping the prepared sludge in a second storage tank to increase the surface area thereof;
  further, the prepared sludge is stored in the third storage tank at a temperature ranging between 30° C. to 60° C. for pumping the prepared sludge to at least one Biological Treatment Plant-I,
  thereafter, the prepared sludge is treated with a fluid i.e. ruminal fluid from the rumen of the cow or a 'Fluid' similar to it, with specific 'Microbes' to form treated slurry in the Biological Treatment Plant-I, wherein Biological Treatment Plant-I anaerobic condition, temperature between 35° C. to 40° C., and controlled PH is maintained therein;
  further, the treated slurry is passed to at least one Biological Treatment Plant-II, wherein the treated slurry is treated with enzymes' of or similar to human digestive systems i.e., pancreatic & intestinal enzymes & bile salts therein, wherein Biological Treatment Tank II anaerobic condition, temperature between 35° C. to 40° C., and controlled PH is maintained therein; and
  thereafter, the treated slurry is treated in anaerobic conditions and in controlled PH with thermophilic bacteria in a Biological Treatment Plant-III, wherein Biological Treatment Tank III anaerobic condition, temperature between 35° C. to 40° C., and controlled PH is maintained therein,
  wherein, upon treating the prepared sludge in Biological Treatment Plant-I, Biological Treatment Plant-II and Biological Treatment Plant-III, the biodegradable waste is converted into rich biological fertilizer and methane gas is librated from tank Biological Treatment Plant-I and Biological Treatment Plant-III, which is collected in a principal gas collector, whole process in BTP is biologically and mechanically enhanced to complete the entire treatment within approximately 48 to 72 hrs.

Typically, wherein the fluid i.e. ruminal fluid from the rumen of the cow or a 'Fluid' similar to it, with specific 'Microbes' is used to disintegrate carbohydrates, proteins and lipids in industries, such as paper pulp industry, textile industry, in dye industry, in preparation of laboratory medias, broths/industry, and the like, further, the ruminal fluid of cow or 'Fluid' similar to ruminal fluid, which is used in the process, contains various types, species of microbes. Controlled action/s of specific microbes on prepared sludge in the BTP I can be conducted to obtain a sludge of specific characteristic, which we can call as 'bulk liquid', which will be useful in many types of industries. The bulk liquid can be useful for medicine production in the pharmaceutical Industry. The bulk liquid can be used in nutritional products like protein powder, vitamins etc., after strict sterile treatments.

Typically, wherein the bulk liquid is extracted from Biological Treatment Plant-I and Biological Treatment Plant-II, which in industries such as in cosmetics production/industry, in essence production/industry, in production of soap like products/industry, in paper and pulp industry, in dye industry, in some industries to treat their hazardous effluents/intermediate or end products, in preparation of laboratory medias, broths/industry, in pharmaceutical industry as any type of animal feed, as cattle feed, biofertilizers/industry & in many other industries, in some industries to treat their hazardous effluents/intermediate or end products, in pharmaceutical industry, as any type of animal feed, as cattle feed, biofertilizers/industry & in many other industries Typically, the prepared sludge from the primary treatment tank is used to prepare herbivore's feed at low cost or feed for carnivore's and omnivore's is prepared depending upon the type of biodegradable waste.

Typically, the prepared sludge from Biological Treatment Tank I is used to prepare perfume or essence or aromatic products.

Typically, fertilizer used for converting barren to fertile land. the Biological Treatment Plant I, Biological Treatment Plant-II, Biological Treatment Plant-III is configured in a single chamber Typically, wherein the a gas collector provided with an exhaust pipe for burning the methane there from.

Typically, wherein the Biological treatment plant II is connected to gas collector for passing gases generated therein.

Typically, wherein the Biological treatment plant I, Biological treatment plant II and Biological treatment plant III is provided with manhole of predefined size at predefined location for regular maintenance.

DETAIL DESCRIPTION OF THE PRESENT INVENTION

The foregoing objects of the invention are accomplished and the problems and shortcomings associated with the prior art techniques and approaches are overcome by the present invention as described below in the preferred embodiment.

Figure 4:
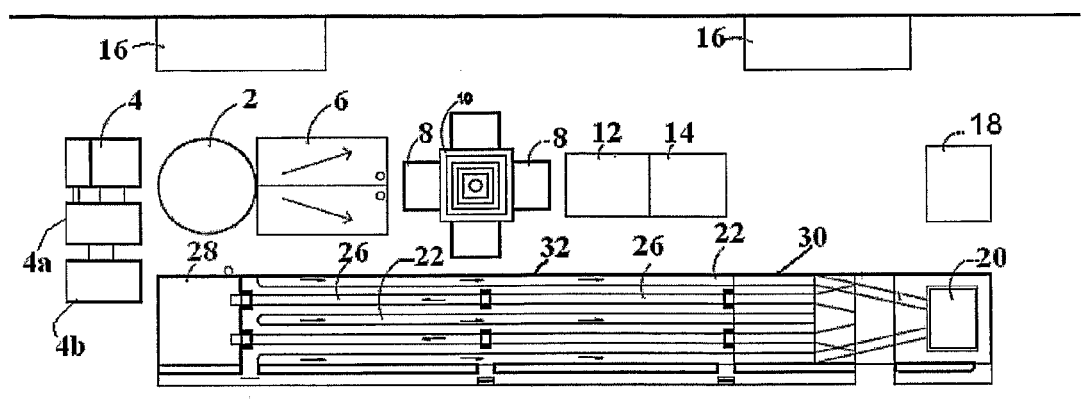
FIG. 4. shows top view of a system for biological treatment of BW including MSW according to the present invention.
Figure 5:
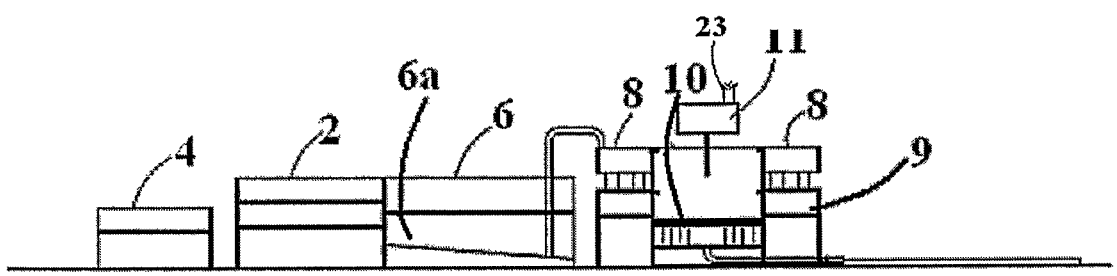
FIG. 5 shows side view of FIG. 3.
Figure 6:
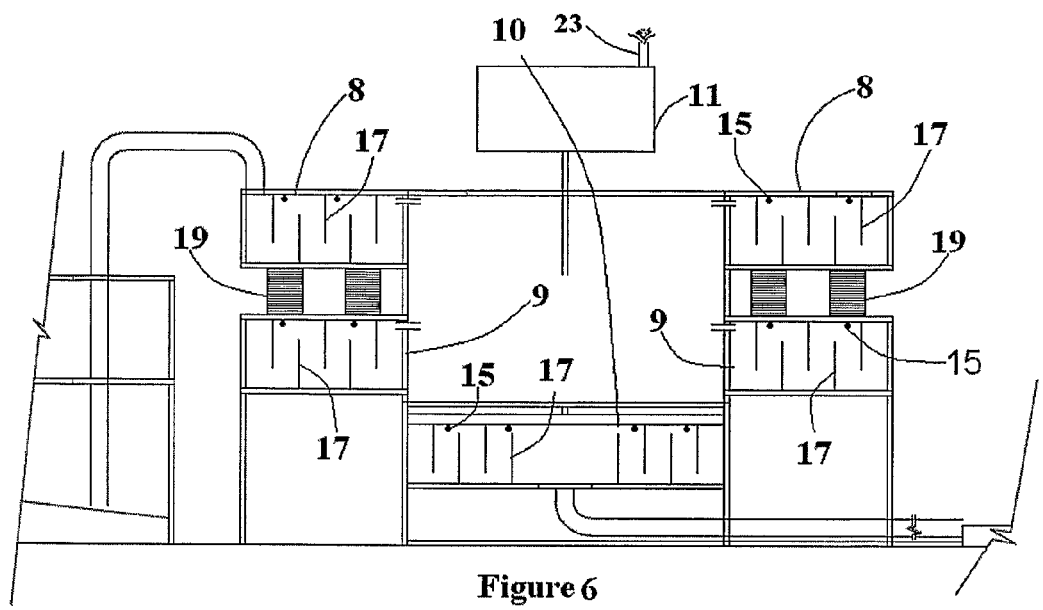
FIG. 6 shows enlarged view of the biological treatment plant I, II and III of the system of the present invention.

Referring to FIGS. 5 and 6 shows a various views of system for biological treatment of biodegradable waste (herein referred as BW) including biodegradable municipal solid waste. The system includes an un-loading platform (20), at least one conveyor belt, the FIG. 4 is shown to include two conveyor belts (26), a magnet chamber (30), at least one separator, in FIG. 4 it is shown to include one separator (32), and first storage tank (28). The unloading platform (20) is provided for unloading the mixed solid waste (herein after referred as SW) collected from various sources. SW is generally collected from various city areas in various containers and unloaded on to the site of the system. The conveyor belts (26) are capable of conveying the SW from the unloading platform (20). The magnet chamber (30) is provided next to the unloading platform (20). The conveyor belts (26) with the SW are passed thought the magnet chamber (30) for separating metal part from the SW. The magnet chamber (30) is provided with strong magnets, which are capable of attracting metals. The separator (32) provided next to the magnet chamber (30). The recyclable inorganic waste is separated from the SW in the separator (32). In an embodiment, the separation is done manually by appointing group of peoples for separating material, such as wood, plastic, small particles, cloths, papers and the like. In another embodiment, the separation is done automatically, by using robotic technology. Further, the first storage tank (28) is provided next to the separator (32). The first storage tank (28) receives segregated BW from SW. This setup may also be installed at various places including that of the urbanized society for processing the BW.

The system also includes a primary treatment tank (2), a second storage tank (6), a third storage tank (6a), at least one Biological Treatment Plant I (8) (Biological Treatment Plant herein after referred as BTP) FIGS. 4, and 5 are shown with four BTP I (8), at least one BTP II (9), FIGS. 4, and 5 are shown with four BTP II (9), BTP III (10), and a gas collator (11). The above mentioned elements of the system may be configured at remote places away form urbanization. The segregated SW form the first storage tank (28) which is located at various places is collected at a point for processing further.

The primary treatment tank (2) receives the segregated BW from SW from the first storage tank (28). The primary treatment tank (2) is capable of separating oil, grease, plastic, small particles and the like from the BW. The primary treatment tank (2) includes a chamber, and a rotor. The chamber is capable of collecting the BW and mixing the BW with hot water having temperature in the range of 70° C. to 140° C. to kill pathogens. The rotor is capable of rotating/churning the mixture of BW with hot water. Addition of hot water leads to heating, thereafter rotating and thereafter allowing natural settling of the mixture for pre-determined hours and the similar process is repeated at least twice, thereby enabling separation of other non-degradable waste from BW to form prepared sludge. The supernatant water consists of non-degradable waste, such as oil, grease and the like, which is further separated and purified in a purification plant (4). The purification plant includes extracted water tank (4), a chlorination tank, aerobic tank (4a), and a pure water tank (4b). The prepared sludge from the primary treatment tank (2) is further dried and compacted to prepare herbivore's feed at low cost or feed for carnivore's and omnivore's is prepared depending upon the type of BW.

Referring again to FIGS. 4 and 5, the system includes the second storage tank (6). The second storage tank (6) is disposed adjacent to the primary treatment tank (2). The second storage tank (6) includes a grinding and chopping mechanism for grinding and chopping the compacted prepared sludge. The third storage tank (6a) is disposed juxtaposition to the second storage tank (6). The third storage tank (6a) is capable of collecting and storing the prepared sludge received from the second storage tank (6) at a temperature ranging between 30° C. to 60° C. at least one Biological Treatment Plant (herein after referred as BTP)-I (8) receives pumped prepared sludge from the third storage tank by means of a pump, wherein the prepared sludge is treated with a fluid i.e. ruminal fluid from the rumen of the cow or a 'Fluid' similar to it, with specific 'Microbes' to form treated slurry therein. Further, anaerobic condition, temperature between 35° C. to 40° C., and pre-defined controlled PH is maintained in the BTP I (8).

The BTP-II (9) disposed juxtaposition to the BTP-I (8). The BTP-II (9) receives treated slurry from the BTP-I (8), and treated with enzymes' of or similar to human digestive systems i.e., pancreatic & intestinal enzymes & bile salts therein. Further, the BTP-I (8) and BTP-II (9) are connected by at least one connecting element (19) to pass the slurry from BTP-I (8) to BTP-II (9), therebetween treated with acid to kill the microbes from BTP-I (8). In an embodiment, the connecting element (19) is a hollow pipe or a tube or passage. Furthermore, anaerobic condition, temperature between 35° C. to 40° C., and pre-defined controlled PH is maintained in the BTP II (9).

The BTP-III (10) is disposed juxtaposition of the BTP-II (9) and BTP-I(8). Further, anaerobic condition, temperature between 35° C. to 40° C., and pre-defined controlled PH is maintained in the BTP III (10).

The BTP-III (10) is capable of maintaining anaerobic conditions for treating the treated slurry with thermophilic bacteria therein received from BTP-II (9). Upon treating the slurry in BTP-I (8), BTP-II (9), and BTP-III (10), the prepared sludge is converted into rich biological fertilizer and methane gas is librated which is collected in a collector chamber (11). In another embodiment, the BTP-I (8), BTP-II (9), and BTP-III (10) include plurality of baffle walls (17) to ensure continuous flow of BW therein. The BTP-I (8), BTP-II (9), and BTP-III (10) also include sprinklers (15) for sprinkling the all the respective treating material of the respective BTP. The sprinklers (15) ensures proper mixing of BW with all the respective treating material. Further, an exhaust pipe (23) is provided on the gas collector (11) for burning the methane there from.

The present invention also includes a method for biological treatment of biodegradable BW including municipal solid waste. The method includes steps of loading the SW on the conveyor belt (26).

Further, passing the conveyor belt (26) containing SW through a magnets in the magnet chamber (30) for separating metal parts from the SW.

Furthermore, passing the conveyor belt (26) containing SW through at least one separator (32). The recyclable inorganic waste is separated from the SW to form BW.

Thereafter, segregated BW is collected in a first storage tank (28).

Further, treating the BW from the first storage tank (28) in primary treatment tank (2). The BW is mixed with the hot water having temperature in the range of 70° C. to 140° C. to kill pathogens and thereafter rotating and thereafter allowing natural settling of the mixture for pre-determined hours and the similar process is repeated at least twice, thereby enabling separation of other non-degradable waste from BW to form prepared sludge. The separated supernatent and extracted water is purified in a water treatment plant as explained above.

Thereafter, after compaction and de-hydration, grinding and chopping of the prepared sludge in a second storage tank (6) to increase the surface area by reducing size of the particles of the sludge thereof.

Further, the prepared sludge is stored in the third storage tank (6a) at temperature ranging between 30° C. to 60° C. and the prepared sludge is pumped and treated in at least one BTP-I (8), BTP II (9) and BTP III (10) as mentioned above.

Further, an underground storage tank (16) is provided to collect purified water from the purification tank and is supplied to the primary treatment tank (2) which may be used as per the requirement of the system.

In an embodiment, the system includes storage for liquid and sold fertilizer (12) and an unloading platform for packed fertilizers (14). The system also includes a washing tank (18) for sorting and recycled material separated from the separator.

In an embodiment, a pusher and a rotor is provided in Biological Treatment Plant I (8), Biological Treatment Plant II (9), and Biological Treatment Plant III (10). The pusher introduces waves in forward direction and the rotor to enhances proper mixing of ruminal fluid or enzymes in the prepared slurry.

Figure 7:
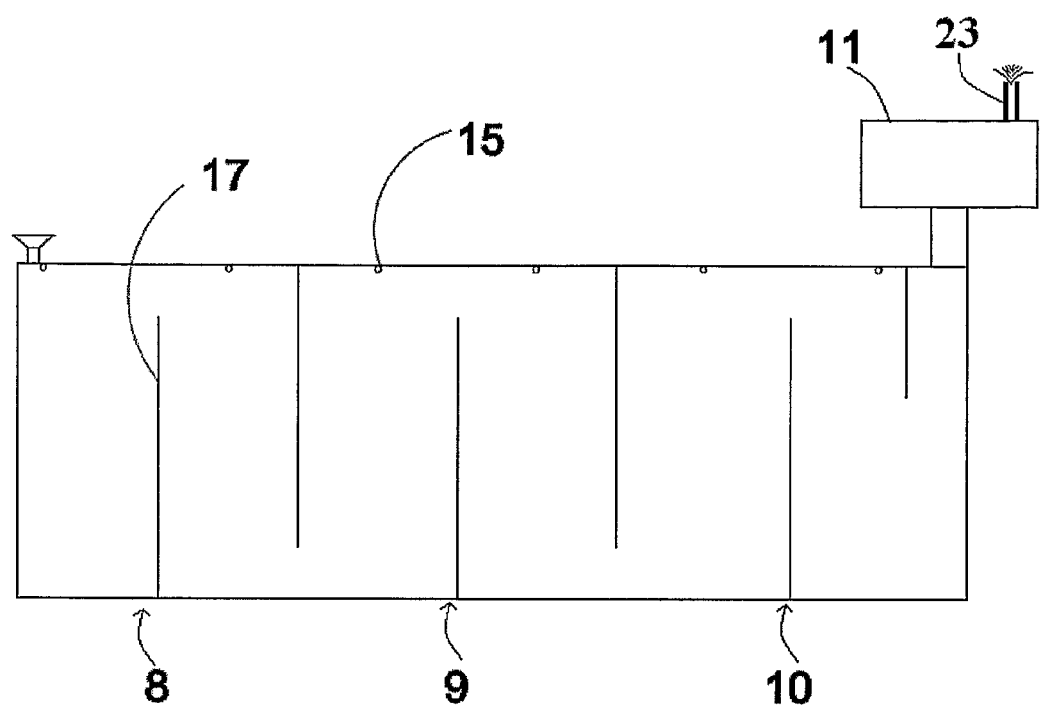
FIG. 7 shows an embodiment of Biological Treatment plant (BTP) of FIG. 6.

FIG. 7 shows an embodiment of Biological Treatment plant (BTP) of FIG. 6. The BTP is includes a chamber having compartments configuring BTP I (8), BTP-II (9), BTP-III (10), and a gas collector (11) suitable for small-scale residential/commercial complexes. Further, an exhaust pipe (23) is provided on the gas collector (11) for burning the methane there from.

Further description is provided only for better clarity of the subject matter of the invention:

The Basic Design and the Total Process of Biological Treatment Plant—BTP—for Treatment of Biodegradable Waste (BW)

We are mainly concentrating on BW which also includes biodegradable matter of municipal waste which will be treated in this BTP Basic Processes of Biological Treatment Plant—BTP They can be summarized as follows:
  The BTP works in two stages—
  In Stage I—Preparation of the sludge
  In Stage II—Biological treatments on the prepared sludge
  Stage I—Preparation of the sludge
  Stage IA—Primary Treatment Tank/Sludge Preparation Tank
  Stage IB—Treatment of extracted water Preparation of the sludge is carried out in the following steps in brief:
  a. Manual/Mechanical separation of Bio degradable waste (BW)
  b. Hydrolysis or softening of biodegradable waste under controlled temperature.
  c. Dehydration by way of compaction and mechanical bio-drying
  d. Chopping and grinding to increase the surface area
  e. Storage of prepared sludge under controlled temperature Preparation of sludge serves the following purposes:
  Hydrolysis or softening of biodegradable waste matter under controlled temperature helps the biological treatments to become easy & fast, as due to high temperature the sludge acts as half cooked food. The pathogens are also automatically killed.
  Due to chopping and grinding of matter the surface area of the particles is increased and thus biological reactions take place to the maximum possible extent A. Details of Stage I A. Activity:—
  In Stage I following activities are followed in series:—
  a. Manual/Mechanical separation of Bio degradable Waste:—
    The Mixed Solid Waste will be brought to the BTP site & weighed on the weighing platform for analytical purposes.
    The Mixed solid waste will be unloaded on the unloading platform in the manual/mechanical separation section.
    This will be conveyed to conveyor belt which will be moving at a very slow speed.
    Initial 10 m of belt will have very high capacity magnets to attract even minute metal objects from the Mixed Solid Waste on the conveyor belt.
    Rag pickers will manually separate out all other types of waste other than bio-degradable waste and only bio degradable waste will be allowed to enter into Primary Storage Tank of Stage I.
    The CST principle (Collection separately-Segregation strictly-Transport separately) should be followed strictly in urban areas, depending upon the characteristics of waste.
  b. Hydrolysis or Softening of Tissue
    The bio-degradable waste (BW) from Storage tank will be transferred to primary treatment tank on weight/volume basis because the process of Hydrolysis or softening of tissue will require specific quantity of water under controlled temperature (preferably 100° C. to kill the pathogenic bacteria).
    Softening of tissue and cleaning of BW to the minute level to have clear BW is done with the help of addition of water under controlled temperature. The mechanical rotor/churner will be in operation to churn the entire volume and this particular activity will be similar to the action taking place in any washing machine, after which the whole volume will be allowed to settle down for some designed hours. This process can be executed 2-3 times depending upon the characteristic of the waste, to get clean and clear bio-degradable waste (BW).
    In this process the Oil, Grease, small particles, wood, plastic pouches or any other material which is not expected to enter the treatment plant will float on the surface of the water and can be separated out easily. The supernatant water containing, oil, grease will be collected in the water treatment tank and will follow a separate process of purification of this extracted water.

c. Compaction & Dehydration

The wet BW will have larger volume due to its water content so it will undergo compaction and mechanical bio-drying process to reduce the volume of clear BW. In this process by way of compaction and mechanical bio drying the total volume will be reduced to approx 60% of its original volume. Collected water after compaction will enter into the Water Treatment Tank and relatively dried material will be ready to undergo the next process of chopping and grinding.

d. Chopping and Grinding Process

The relatively semi-dried material will be transported to the chopping and grinding floor to undergo chopping and grinding activity to increase/maximize the surface area of the particles, to have particles of minute size for effective operation of biological treatments. At this stage the sludge can be called as 'prepared sludge'.

e. Storage of Prepared Sludge

This prepared sludge is stored in the final storage tank of Stage I activity. This storage tank of the prepared sludge will be maintained under controlled temperature by mechanical means preferably at 40° C. to prevent the growth of pathogenic bacteria.

Thus, the sludge is ready to enter the storage Tank and further into Stage II process, of the biological treatment plant, i.e., BTP Stage-II.

Stage I B.—Treatment of Extracted Water

All Extracted & Separated water will be stored in the water Treatment Tank and from here, after settlement the supernatant having oil and grease as major content will be taken to a separate tank for its treatment and the remaining water will undergo Aerobic treatment by way of Aeration and will be treated with the help of specific bacteria. The oily water will be separately treated.

During the Stage-I A sub-activity (b) & (c) the Extracted & Separated water will be released from the sludge and will be collected in the same Water Treatment Tank & will undergo the same treatment process.

Treated water from the tank will be collected in the Treatment Tank for Chlorination.

Relatively pure water will be stored in the disposal tank and will be available for natural disposal or for the re-circulation in the same plant.

Stage II: Biological Treatments on the Prepared Sludge

Thus, the object of invention is that when all the biological reactions of Stage I & II are placed in series and allowed to follow the same path as natural biological actions, then the enriched biological fertilizer, CH4 i.e. methane, CO2, H2O, & NH3 are obtained as final end products, from Biodegradable Waste and this is the basic concept of the BTP i.e. BIOLOGICAL TREATMENT PLANT. In the BTP the whole process, is biologically & mechanically enhanced to complete its total cycle within approximately 24-36 hours The Biological Treatments of BTP are carried out in three Different Plants, based on different principles of processes, the plants are called:

1. Biological Treatment Plant I-BTP I
2. Biological Treatment Plant II-BTP II
3. Biological Treatment Plant III-BTP III Thus, the combination of biological process by using 'Fluid' i.e. Ruminal fluid from the rumen of the cow or a 'Fluid' similar to it, with specific 'Microbes', Enzymes' of or similar to human digestive systems i.e., pancreatic & intestinal enzymes & bile salts, and anaerobic digestion by *Thermophilic bacilli*, all in series to treat the biodegradable waste (BW), are the basic processes involved in this Biological Treatment Plant i.e., BTP, in BTP I, II, III of it and this is the main object of invention of BTP.

The another novelty and object of invention of this process is that different 'modules' of this chain/series of process can be used either singly or in variable combinations according to the input ingredients of BW & the need of action of any module.

Main Materials used in the BTP I, II, III

1) To complete this series/chain of processes biologically, following materials are used under anaerobic conditions, controlled temperature, & specific PH, in different BTP Tanks:

1) In BTP I: The 'Fluid' i.e. Ruminal fluid from the rumen of the cow or a 'Fluid' similar to it, with specific 'Microbes', is used.

2) In BTP II: 'Enzymes' of or similar to human digestive systems i.e., pancreatic & intestinal enzymes & bile salts & are used 3) In BTP III: '*Thermophilic bacilli*', are used Different combinations of all the materials according to the process requirement can be done.

The Main Functions and Aims of BTP I, II & III

BTP I

In this plant with the help of biological actions of 'Fluid' 'microbes', The tough & complex carbohydrates of plant material are completely treated, and converted to Methane, CO2, & H2O directly, the proteins of all types are converted to Ammonia directly & lipids are also converted to CH4, CO2 & H2O. These reactions occur in a very short span of time i.e., just 6-12 hours. In none of the existing treatments for biodegradable waste, such fast & complete reactions occur.

BTP II

This plant is mainly required for the treatment of remaining untreated biodegradable matter of animal origin & the carbohydrates, proteins, lipids of the dead microbes. They are treated in this tank to obtain simple end products i.e., glucose/glactose, basic amino acids and fatty acids, in just 12-24 hours.

BTP III

Till now all types of carbohydrates, proteins & lipids present in any biodegradable waste are treated and converted to end products i.e., glucose/glactose, basic amino acids and fatty acids, in just 24-36 hours but these products cannot be accepted by plants directly through soil (the treatment of soil bacteria on them is normally needed), that is why the BTP III is needed in which by anaerobic digestion with the help of *thermophilic bacilli*, the end products produced are—rich biological fertilizer, Methane, Ammonia, CO2. These products are fastly & more easily accepted by the soil bacteria, also the processing time of bacteria is reduced. then these are absorbed by plants from soil to prepare their food and thus the end products needed for Recycling Stage III of biodegradable matter, are finally produced.

Thus the aim of BTP I+II+III is to treat BW, completely. The treatment is completed in just 24-48 hours.

Different Mechanical Processes used in all the BTP's (BTP-I, II, III)

Mechanical unloading platform

Conveyor belt for the segregation of the mixed solid waste

The mechanical rotor/churner will be in operation to churn the entire volume, during the process of Hydrolysis or softening of tissue during preparation of sludge Compaction and mechanical bio-drying process to reduce the volume of clear BW Chopping and grinding activity to increase/maximize the surface area of the particles Biological Treatment Plant the prepared sludge is added on weight basis i.e., Kg/Hr. Depending upon the capacity of plant, by mechanical means.

Prior to the treatment this particular chamber is mechanically de-oxidized since the entire process is anaerobic.

In BTP I—The baffle walls & rotator and churner action to allow the slurry of prepared sludge to move ahead.

The BTP II & III are provided with baffle walls to move the slurry ahead.

All BTP's will have the mechanical (sprinkler) systems fixed in the tanks to add (sprinkle) the 'fluid' or 'enzymes' or '*thermophilic bacilli*' at periodical level as per the biological requirement of the sludge. of the respective tanks Mechanically controlled outlets for each BTP are provided

SUMMARY

Thus, any processing plant for the treatment of biodegradable waste, BW, designed on the basis of N2N (Nature to Nature) theory, using materials as mentioned above and use of processes as mentioned in BTP's will have following advantages:

The entire process of treatment/bio degradation will be complete in 24-48 hours.

As the BTP processes (Biological reactions) are complete, half treated or hazardous products are not produced. Every product is useful to either plants or to nature.

Due to completion of process in such a short time span the amount of nutrients which are absorbed from the nature by the plants on a daily basis will be re circulated in the nature in a natural way on a daily basis.

The entire amount of gases produced during the BTP processes are collected in the collecting chambers since the entire process is in a closed container.

Will have the maximum volume of CH4 available to make the plant self sustainable, by use of methane in different ways.

Rich organic fertilizers in the powder and in the liquid form will be obtained.

More land will be available, as the area wasted in landfills will be saved, thus we can increase the carbon sink The letachae formation will be absent, which will ultimately prevent the loss of soil and natural water sources.

Will help in progression towards zero garbage city and zero garbage earth.

Will prove to be helpful to reduce the green house effect in the long run.

From here onwards 'Tank' means the containers used in all the processes of BTP

Biological Treatment Plant I, TANK-I (BTPI-TANK-I): General

Substrate used in BTP I, Tank-I

The prepared sludge will come in this tank for biological treatment.

The prepared sludge is thus the biodegradable organic material consisting of mixed type of constituents of both plant & animal origins including biodegradable MSW.

Thus ultimately this prepared sludge will consist of mainly CARBOHYDRATES, PROTEINS & LIPIDS, whatever may be its sources.

Basics of the BTP I, Tank-I

This will be a closed tank, thus creating strictly anaerobic environment

The PH of this tank will be −5.5-6.5.

Temperature will be controlled around 37-40° C.

The ingredient will be added evenly & periodically as per biological need, by mechanical means.

Baffle walls are provided in this tank and are such designed to act, similar to the motions of the stomach, for proper mixing of the sludge & to fasten the process.

Biological Material used in the BTP I, Tank-I

The Material used in this tank is cow's Ruminal fluid or 'Fluid' similar to cow's Ruminal fluid (we will call it as 'Fluid' here onwards), containing 'microbes'.

'Fluid' used in this tank, Contains millions of microbes ($10^{12}$), of around 200 species, most of which have the capability of multiplying every 13 minutes, which act continuously on various food constituents.

The 'Microbes' from this 'Fluid' (will be called as 'Microbes' hereonwards) are obligatory anaerobes, need carbon dioxide, nitrogen, sodium and VFA to grow &, PH of approx. 5.5-6.5, & temperature of 37-40° C.

'Microbes' from this 'Fluid': Are bacteria, protozoa, fungi, archea and viruses. Bacteria, along with protozoa, are the predominant microbes and by mass bacteria, account for 60% of total microbial matter.

The microbes that are present in the fluid complete their one cycle of action approx. in 6 to 8 hours.

Biological Actions Taking Place in BTP I, Tank-I are

I. Microbial Actions Taking Place in BTP I:

The millions of 'Microbes' from this 'Fluid', start their action on all the food constituents, with their various enzymes, millions of Microbes break down the constituents of matter i.e., carbohydrates, proteins, lipids into their simpler forms. Methane is produced during the process. (85% of methane is formed from organic matter).

Few Specialties of the Microbes are—

They convert toughest food carbohydrates like cellulose, hemi cellulose, xylose, pectin, and gums from complicated forms to simpler forms. They complete about 70% of cellulose digestion. They also digest Lignin. (It is not a carbohydrate, but is major component of many plant cell walls (wood, hulls, straw overfipe hays etc.), & is bound to cellulose and hemi cellulose, due to lignification plant cells/fibres become strong & resistant. It is indigestible & thus doesn't allow digestion of cellulose & hemi cellulose)

They act on all types of proteins, non protein nitrogen (NPN) & to some extent on lipids, plant lipids. The microbes secrete various types of enzymes which are capable of acting on all types of food components, as mentioned above. They can synthesize NPN (urea, ammonia), amino acids, & few vitamins like vitamin B12.

The 'Microbes' are of various types, & perform different actions. Few major microbes & their functions are as follows:

Fiber-Digesting (or cellulolytic) Bacteria's: act on cellulose, hemi cellulose, & pectin. They digest it & produce acetic acid (acetate), butyric acid (butyrate), propionic acid (propionate), hydrogen, & CO2.

Starch and Sugar-Digesting (or Amylolytic) Bacteria: They act mainly on Sugar, Starch, Peptides, Amino Acids & by Fermentation Produce Propionate, Butyrate, Acetate, Lactate, Hydrogen (H2), Carbon Dioxide (CO2)

Lactate-Using bacteria: use lactate produced

Hydrogen-Using (or Methanogenic) Bacteria use carbon dioxide and hydrogen & produce Methane Rumen protozoa: They eat other microbes, and degrade and digest feed carbohydrates, especially starch and sugars, and protein. The rumen protozoa produce fermentation end-products similar to those made by the bacteria, particularly acetate, butyrate, propionate, and hydrogen.

Rumen Fungi: they hydrolyse some ester linkages between lignin and hemicelulose or, and help to break them down, thus making cellulose, hemi cellulose available for treatment.

Rumen Archaea: Are mostly methanogens and produce methane. Most of the hydrogen produced by bacteria, protozoa, and fungi is used by these methanogens to reduce carbon dioxode to methane. Archaebacterias consume the byproducts Acetate, H2 & CO2 and produce Methane. The methanogens present in the 'Fluid' along with other microbes digest cellulose & produce methane (can produce upto 400-600 liters of CH4/day, from approx. 40 kg of organic matter)

II. Details About the Processes of Breakdown of Different Food Components i.e., Carbohydrates, Proteins & Lipids in the BTP I are as Follows:

Basic food components of Substrate: whatever may be its source are

Carbohydrates: all types of carbohydrates i.e., structural (hemi cellulose, cellulose), non structural (starch, dextrin, amylose, amylopectin), all types of sugars (maltose, sucrose, lactose, cellbiose, glycogen, mucopoly saccharides, etc.), complex carbohydrates (xylose, pectin, gums), chitin, lignin etc.

Nitrogen containing compounds: proteins—All types of simple, conjugated, derived proteins, peptides, and amino acids.

Lipids—simple (triacylglycerol), which is found in dietary fats & oils, fatty acids, cholesterol, phospholipids, plant lipid.

Non protein nitrogenous compounds: urea ammonia.

Minerals & vitamins

Thus, a wide range of organic matter present in biodegradable waste is processed here.

III. Three Types of Biological Processes Occur in BTP I, Tank-I a) Hydrolysis—microbial enzymes (cellulose, hemicelluloses, protease, lipases etc.) act on all types of carbohydrates, proteins, lipids, non protein nitrogen compounds. & the bonds between large polymers are broken and simple monomers are formed.

b) Anaerobic fermentation—

Sugars—many bacteria in the 'Fluid', can Ferment sugar (glucose) to acetic acid directly without using ethanol as an intermediate or to VFA's (volatile fatty acids).

Proteins (amino Acids) are fermented to ammonia

Glycerol (lipids) fermented to VFA's

H2 & CO2 formed during process are also converted to Acetic acid

Main fermentation reactions by anaerobic microbes are as follows:

From Sugar—Acetic Acid is formed directly: (C6H12O6=3CH3COOH directly)

From Sugar—VFA's are formed, which are then converted to—Acetic acid

CO2, H2 formed during the process are also converted to—Acetic acid [2CO2+4H2=CH3COOH (acetic acid)+2H2O]

c) Methanogenesis—The methanogenic bacteria (methanogens) present in the 'Fluid', convert acetic acid to methane. They use hydrogen and carbon dioxide (H2 & CO2) to produce methane thus lowering the amount of hydrogen gas, which is formed during all above reactions in the tank.

[Methanogenesis occurs as follows

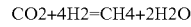

CO2+4H2=CH4+2H2O

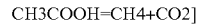

CH3COOH=CH4+CO2]

IV. Biological Processess in Detail in BTP I, Tank I

IVA. Breakdown of Carbohydrates: Detailed Process

All types of carbohydrates are hydrolyzed to—glucose & simple sugars by microbial enzymes.

Fibre which is a complex carbohydrate is composed of cellulose, hemi cellulose, and lignin, pectin, gums are easily digested, & lignin which is resistant is also digested.

The microbial enzymes like cellulose, hemicelluloses etc act on all types of linkages in carbohydrates i.e., α-1-4/1-6, β-1-6 etc and break polymers to monomers. Even the ester linkages of lignin are also hydrolyzed by fungi present in the 'Fluid'

The glucose & simple sugars are then transported into the microbes.

Immediately after formation, glucose & sugars are fermented to Volatile Fatty Acids (VFA) i.e., acetic acid, propionic acid, butyric acid & to some extent to lactic acid, is butyric & isovaleric acids, or converted directly to acetic acid. VFA's are further converted to acetic acid (all in the presence of ammonia (NH3), & vitamin B12).

Also H2 & CO2 are formed during the process

From H2 & CO2, Hydrogen using bacteria, by fermentation, form methane [4H2+CO2=CH4+2H2O].

Methanogens in the 'Fluid'; form acetic acid & formic acid. From both the acids & H2, CO2, they form CH4 i.e., methane.

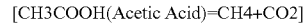

[CH3COOH(Acetic Acid)=CH4+CO2]

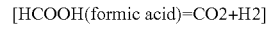

[HCOOH(formic acid)=CO2+H2]

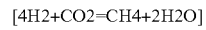

[4H2+CO2=CH4+2H2O]

IV B. Breakdown of Proteins: Detailed Process

All types of proteins & NPN compounds are hydrolyzed to peptides and amino acids by proteolytic microbial enzymes polypeptide bonds are broken and free amino acids are formed.

By microbial fermentation, amino acids are broken down into ammonia, methane, CO2, and simple amino acids.

Peptides, amino acids, ammonia, & other sources of nitrogen in the sludge can also be directly used by the microbes without hydrolysis.

The ammonia formed is further used by microbes to form their body protein i.e., amino acids, composing of essential, nonessential amino acids, Approx. 60% of protein is used in the form of ammonia by microbes Microbes also release enzyme 'urease' which converts urea to ammonia [urea=NH3+CO2]

Thus from every type of nitrogenous feed (amino Acids, amides, urea & NPN). Ammonia is finally produced with the help of various microbial enzymes.

IV C. Breakdown of Lipids: Detailed Process

Lipids of animal origin are fats (solid) & that of plant origin are vegetable oils (liquid). 80% of fat are TAG's (triacylglycerol).

'Microbes from the 'Fluid', act on lipid in three steps—

1. Hydrolysis—during which from TAG fatty acids are formed

2. By hydrogenation—unsaturated fatty acids are converted to saturated fatty acids (i.e. fatty acids with no bonds), by microbial enzyme 'hydrogenise', in anaerobic condition.
3. Fermentation—'Microbes' ferment glycerol, galactose to VFA's by and they are then converted to Acetic acid.

Thus:
   TAG's are hydrolyzed to glycerol & fatty acids. The Fatty acids by microbial action are saturated & Then fermented to VFA's & short chain fatty acids
   Thus Finally Propionic acid, Acetic acid, Butyric acid (VFA's) are converted to Acetic acid
   Most of the lipids present in plants are galactolipids, which have glycerol—sugar linkage as beta galactosidic sugar linkage. Microbes contain enzyme 'galactosidases', which break (hydrolyze) galactolipids into glycerol & galactose which are further fermented to VFA's (glycerol—mainly to propionic acid & galactose mainly to acetic & butyric acids)
   By methanogenesis Acetic acid is converted to methane and CO2
   Long chain fatty acids are not acted upon and transferred to BTP Tank II
   Lipids are partly broken down in this tank
   Vitamins: Microbes synthesize many vitamins such as vitamin B12, which are helpful to their metabolic activities
   Minerals: Minerals are absorbed by the microbes End roducts of BTP I are:
   After the breakdown of carbohydrates, proteins, lipids present in the Biodegradable organic matter of BW, by the action of the microbes, Acetic acid, VFAs, Amino Acids, Ammonia, Methane and CO2, water, & enriched Biomass are produced. VFA's are then converted to acetic acid, while amino acids are converted to ammonia.
   Thus Ammonia, Methane, CO2, water & enriched biomass are the Final end products of BTP I, Tank I.

Figure 3:
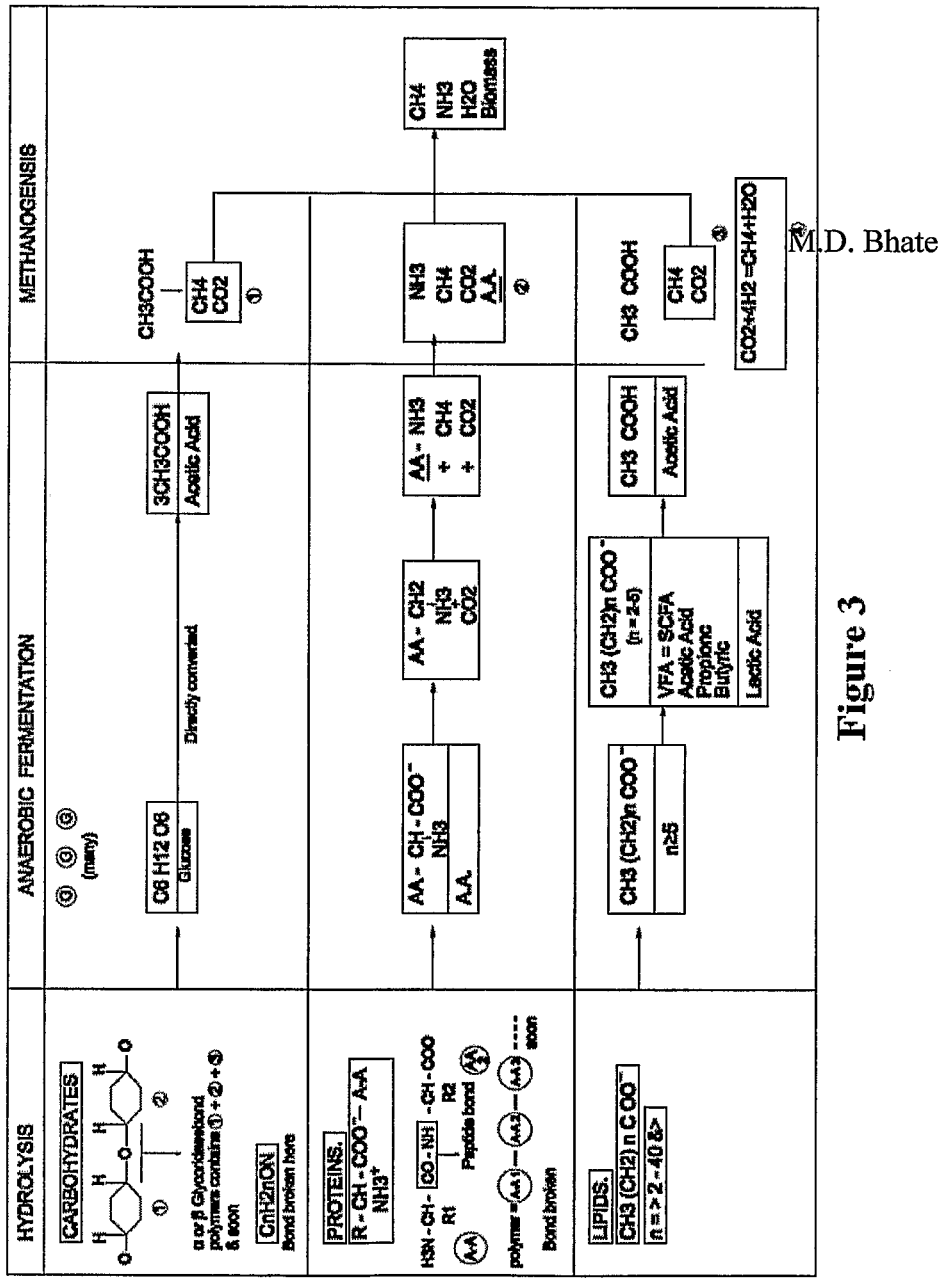
FIG. 3 shows a chart of chemical reaction in BTP-I.

Actual biological process of BTP I as shown in FIG. 3.

Figure 1:
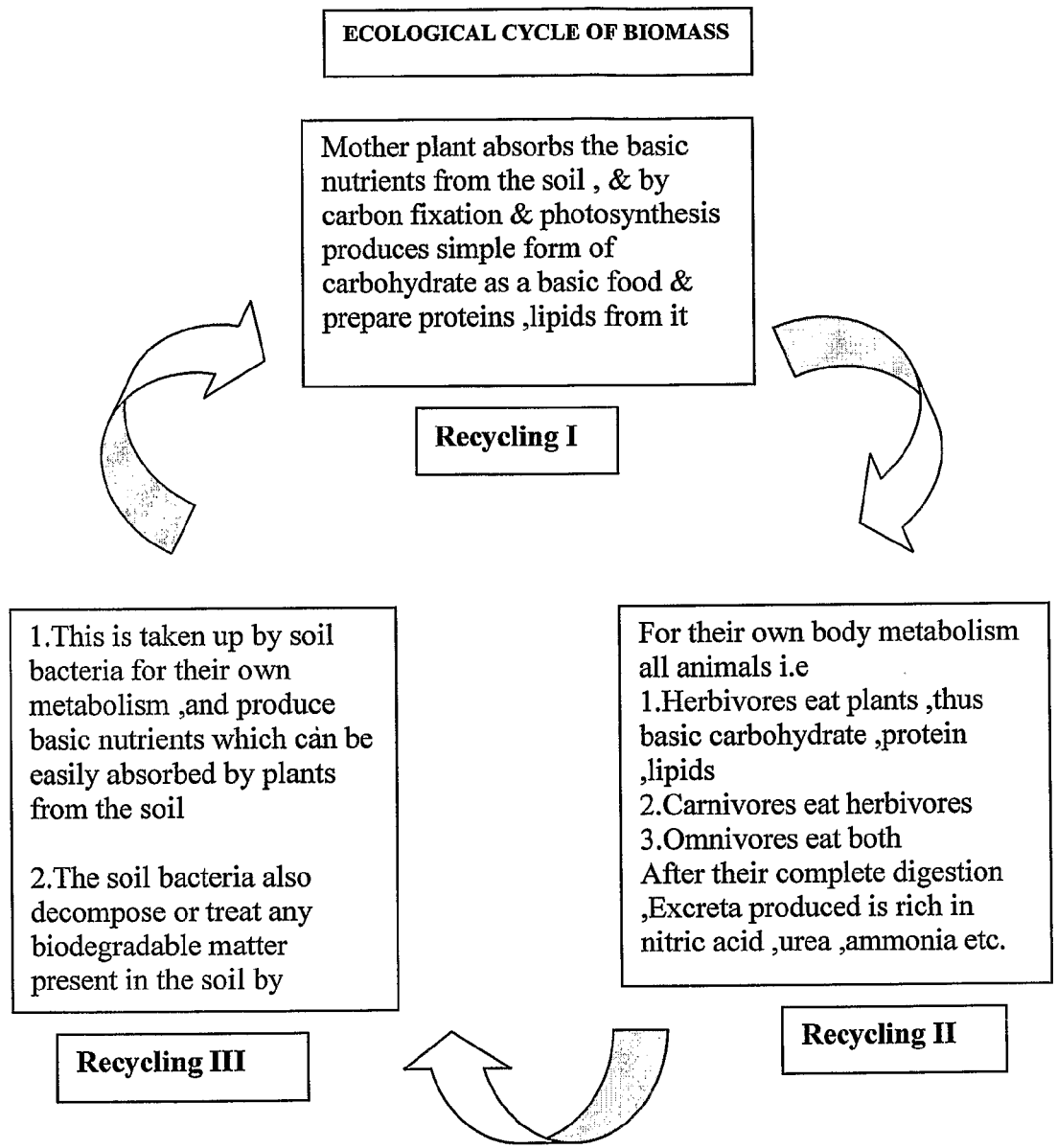
FIG. 1 explains the ecological cycle of biomass.
Figure 2:
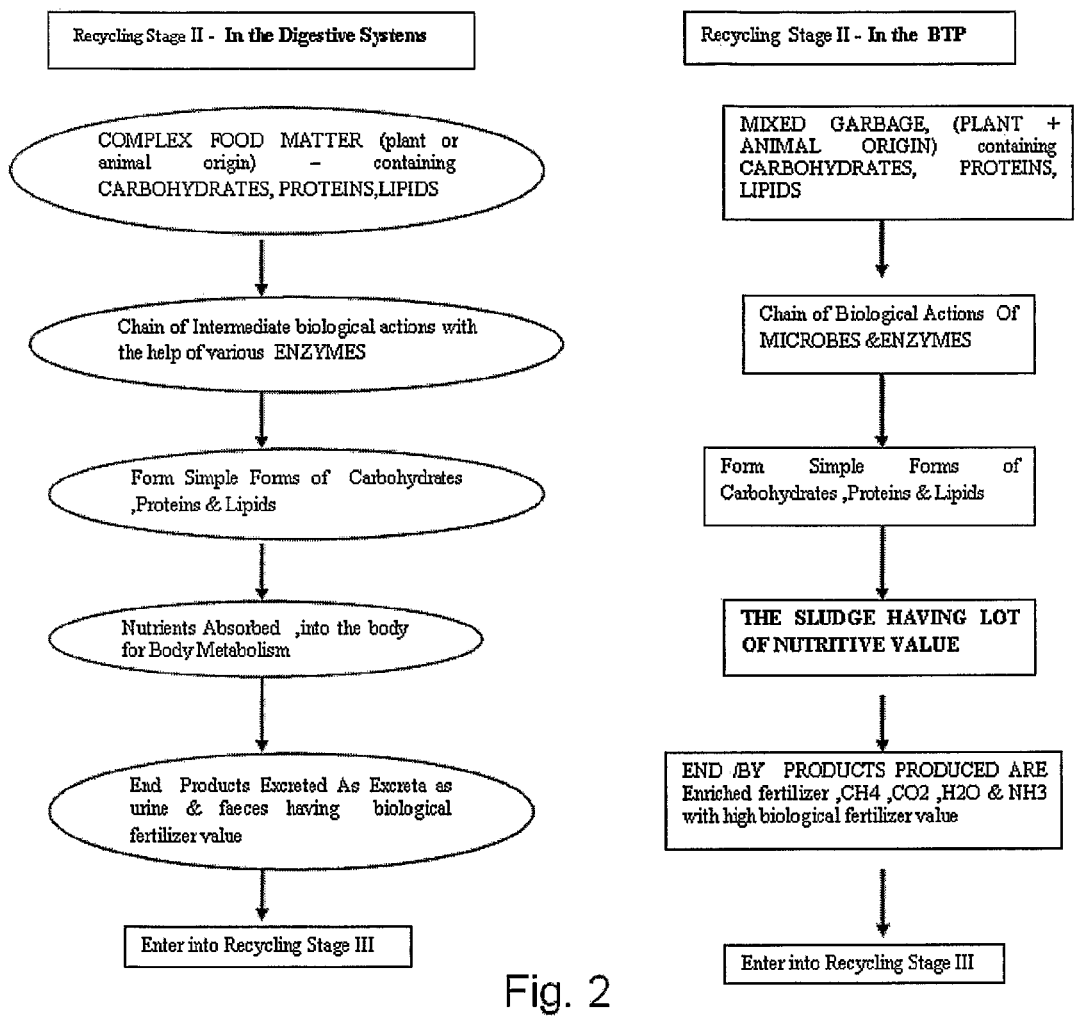
FIG. 2 shows comparison chart in digestive system and in the BTP.

Intermediate Path
   Treated sludge from the BTP I, Tank I is allowed to enter through this path, before entering the BTP II tank
   Mechanical sprinklers are used to make the PH acidic
   The 'Microbes' die if exposed to acidic PH of around 2-2.5 (or Oxygen).
   Thus the PH of the sludge is made acidic, in this intermediate path, so the microbial life comes to an end. This is done because the microbes don't have any major role to play in the further process i.e., in the BTPII-Tank II.
   After microbial death the dried debris of microbial mass contains 40-50% crude proteins which is more than 70% digestible which when passed to the BTP II, Tank II, will be treated as proteins and broken down further.
   Microbial lipids of dead microbes which go to BTP II, Tank II will contain approximately, 70% free fatty acids (FFA) & 30% phospholipids Refer FIGS. 1 and 2. Biological Treatment Plant II-Tank II (BTP II, Tank II)

Substrate used: Treated sludge from the BTP I, Tank I, after its passage through inter mediate path comes to this tank
   In this BTP II, Tank II, biological actions of Enzymes from the Human Digestive System or similar to them, continue further breakdowns of the food constituents, formed in the previous tank & those which remain untreated in the previous tank. (i.e lipids, proteins of animal origin &constituents of bacterial mass)

Basics of the Tank
   This will be a closed tank, thus creating anaerobic environment
   The PH of this tank will be Alkaline PH (7.1-8.2).
   Temperature will be controlled around 37-40° C.
   In the BTP II, TANK II the baffle walls are provided to have the same effect as that of motions of the intestine for proper mixing & to fasten the process
   The ingredients, are added evenly & periodically with the help of sprinkler system as per the biological need, by mechanical means.

Ingredients added to this tank are 'Enzymes' of or similar to human digestive system i.e., pancreatic & intestinal enzymes& bile salts, (will be called 'Enzymes' here onward)

Biological Actions Taking Place in BTP II
   I. In this biological tank mainly lipids and proteins of animal origin and contents from the previous tank which need further breakdown (i.e., protein & lipid content of dead microbial mass) are treated.
   In this BTP II, Tank-II all the enzymes, i.e., Human Pancreatic enzymes, small intestinal enzymes & bile &/or similar enzymes i.e., 'Enzymes' are added & they together act on different constituents present in the tank.
   These 'Enzymes' are capable of breakdown of all food components completely to the simplest forms.
   Only cellulose, hemi cellulose, xylose etc., cannot be broken by them which are already treated by 'microbes' of 'Fluid' in the BTP I, Tank I.

II. Biological Processess in Detail in BTP II
   Details about the Processes of Breakdown of Different Food Components i.e., Protein, Carbohydrate & Lipids are as Follows:
   'Enzymes' like Pancreatic & Intestinal enzymes act on substrate here. They are a group of many types of enzymes, each or many of them are allotted for breakdown of specific component/s or intermediate product/s of food components II A. Protein Breakdown in BTP II, TANK II—In Detail
   All types of proteins are polymers of amino acids, linked to each other by a 'peptide bond' amino acids are a compound containing two functional groups, i.e., amino (NH2) & carboxyl (COOH) groups. During the treatment, the peptide bonds are broken converting polypeptides first to lower peptides & finally to amino acids
   'Enzymes' involved in this process are a group of enzymes as follows:
   Pepsin—breaks the peptide bonds
   Pancreatic proteases: Chymo Trypsin, Carboxy peptidases & elastases which are activated by trypsin.
1. Trypsin, chymotrypsin & elastase are endopeptidses, which break the internal peptide bonds
2. Carboxy peptidases are exopeptidases act on COOH terminal of Amino Acid (A.A)
   Small Intetinal enzymes—Enteropeptidase, Aminopeptidases, Dipeptidases, Nucleases/polynucleotidase, Nucleotidase, Nucleosidase.

The Aggregate Actions of Different Enzymes are
   Trypsin & Chymo Trypsin, Carboxy peptidases of pancreatic enzymes, Aminopeptidase, Dipeptidases of small intestinal enzymes and pepsin convert polypeptides first to lower peptides & finally to amino acids.
   The combined action of pancreatic proteases results in the formation of free amino acids & small peptides with 2-8 amino acids.

All small intestinal enzymes as treated below undergo following actions:—

Ribonuclease & Deoxyribonuclease—convert DNA &RNA to Nucleotides

Polynucleotidase—convert nucleic acid to nucleotides

Nucleotidases—convert nucleotides to nucleosides

Nucleosidases—convert nucleosides to pentose, purine & pyrimidine bases

II B. Carbohydrate Breakdown in BTP II, TANK II—In Detail:

Carbohydrates in this tank will be

Monosaccharides—MS (e.g. glucose, galactose, fructose, xylose, mannose, etc., out of which MS like xylose cannot be digested by 'Enzymes').

Disaccharides—DS, made up of 2 MS (e.g. maltose, sucrose, lactose, cellobiose, etc., out of which 'Enzymes' cannot digest cellobiose)

Oligosaccharides, made up of 2-10 MS.

Polysaccharides PS made up of repeat units of MS held by glycosidic bonds which are $\alpha$ or $\beta$ 1-4 or 1-6 bonds (e.g. starch [which is made up of amylose & amylopectin,/Dextrin & isomaltase are breakdown products of starch], glycogen, cellulose etc., out of which 'Enzymes' cannot digest cellulose).

'Enzymes' involved in this process are a group of enzymes as follows:

The pancreatic & small intestinal enzymes, contain enzymes which can digest most of the carbohydrates. Each enzyme is product specific The enzymes are: 1. Pancreatic Amylase—Pancreatic amylase acts specifically on $\alpha$1-4 glycosidic bonds of polysachharides like Starch & glycogen.

Oligosacharidases—e.g. $\alpha$ glucoamylase acting on amylose.

Disaccharidases e.g. maltase, sucrase, lactase which act on maltose, sucrose, lactose, respectively.

The Aggregate Actions of Different Enzymes are

Thus pancreatic & small intestinal enzymes convert:

Polysaccharides (Starch,Glycogen) to Disaccharides (Maltose, sucrose, isomaltose) & Oligosaccharides, which are finally converted to Monosaccharides i.e., glucose, fructose & galactose Maltase—converts Maltose to glucose Sucrase—converts sucrose to glucose Lactase—converts lactose to glucose, galactose II C. Lipid Breakdown in BTP II, TANK II—In Detail Lipids are organic substances, relatively insoluble in water & are Esters of Fatty acids. The lipids present in the tank are similar to dietary fat of which majority is—Triaceyl glycerol (90%) & Phospholipid, Cholesterol, Choesteryl Esters, free fatty Acids (in all 10%)

Lipids are insoluble in water while enzymes are soluble, which is the problem in their process of breakdown.

Which is overcome by: Emulsification—By bile salts, which increase surface area of action & decrease surface tension, thus dispersion of lipids occurs, formation of micelle helps the action of lipase on lipids Enzymes involved in the breakdown of lipids are:

Pancreatic Lipase, Cholesteryl Ester Hydrolase, Phospholipase A2

Finally Aggregate Actions of Different Enzymes Are

Pancreatic Lipase—Act on TriAceylGlycerol (TAG), cholesterol & phospholipids. Long chains of lipids with more than 10 carbon are probably broken producing monoaceyl glycerol & Free Fatty Acid (FFA).

Lipase converts Tricylglycerol—to Fatty Acids, mono & diacyl glycerol &glycerol.

Cholesteryl Ester Hydrolase—convert cholesteryl ester to cholesterol

Phospholipase A 2—convert phospholipids to Fatty Acids (FA)+glycerol+phosphoric acid+choline Action of Bile: Bile salts emulsify fat.

End Products—IN BTP II, TANK II

Thus end products of all above food components, after going through different chains of breakdowns are:

Carbohydrates along with glycogen are converted finally to Glucose

Proteins are converted finally to Amino Acids

Lipids are converted finally to Fatty Acids & Glycerol

Thus complex forms of all the components are completely broken into simplest form into this BTPII, Tank II.

Chart. (1, 2, & 3) the Diagrammatic Representation of Breakdown of Carbohydrates, Proteins &Lipids by 'Enzymes' of or similar to human digestive system i.e., pancreatic & intestinal enzymes & bile salts in BTP II are as follows:

Biological Treatment Plant III, Tank III-BTPIII, Tank III—Anaerobic Digestion

Basics about methanogenesis, which takes place in this tank, as a part of one of the process of anaerobic digestion Methanogenesis: is the process of formation of methane by microbes known as methanogens, in anaerobic conditions. It is one of the steps in the process of anaerobic digestion. In nature any biodegradable material undergoes anaerobic digestion, but it is a very slow process taking months, even years for biodegradation. Methanogens play a vital ecological role in efficiently removing the semifinal products of decay i.e., hydrogen, CO2 & thus are important in the carbon cycle Substrate: The sludge from BTP II, Tank II after its completion of process is a substrate here Basics of the Tank This will be a closed tank, having an anaerobic environment & controlled temperature (temperature is controlled/maintained at 40° C.).

Specific type of Thermophilic Bacteria will be added to it, which can sustain very high temperature as well. At the controlled temperature of 40° C. Thermophilic Bacteria are eight times more active.

In the tank the baffle walls are provided to have the same effect as that of motions of intestine for proper mixing.

Material added to this tank is specific *thermophilic bacilli*

Biological Actions Taking Place in the BTP III

The Thermophilic Bacteria are added to hasten the process of methanogenesis.

Anaerobic Digestion will completely breakdown all the matter from the previous tanks, along with the cell material of dead microbial debris, if present—to methane, water and enriched bio-fertilizer & will remove any excess of unwanted hydrogen produced during all previous reactions.

Methane generated during the process of methanogenesis will be collected.

End product; Enriched biofertilizer, Methane, NH3 & water

The diagram explaining The process of anaerobic Digestion is as follows:

Anaerobic digestion is series of processes in which micro organisms breakdown biodegradable material in absence of oxygen The final products of all the above processess are so simple as follows. They can be easily absorbed into the soil through fertilizer and the gases are returned to the atmosphere. They are:—

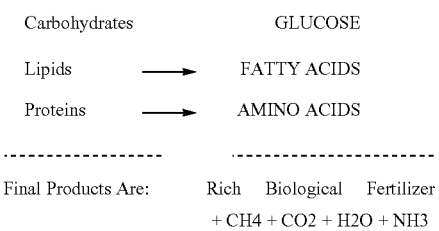

Final Products Are:   Rich  Biological  Fertilizer
                     + CH4 + CO2 + H2O + NH3

Time required for the entire process of BTP, Biological Treatment Plant:
I) Stage I—The process of preparation of sludge—approx 24 hours
II) Stage II—Biological Treatment processes on the prepared sludge
  BTP—I—12 Hours
  BTP—II—12 Hours
  BTP—III—24 to 48 Hours
  Total—48 to 72 Hours
  Thus if Stage I and Stage II activities are in series on the same site, the ultimate end product will be available in 72 hours and if the stage I activity is taking place at collection centre then the ultimate end product can be made available in 48 hours. Thus the entire process can be completed in 24 hours and once this entire cycle is set, then the entire biodegradable waste collected from the collection point of the city can be converted into natural biological fertilizer in 72 hours. Since it is a continuous process another set of prepared sludge can be added everyday and the same quantity of fertilizer can be obtained every day and so on.

By Products Which can be Obtained/Removed from Various BTP Tanks are as Follows:
  General: All the intermediate & end products can be commercially used in various industries by various ways thus making the process cost effective.
  Fertilizer: Fertility of the soil is enhanced due to the use of enriched end products, i.e., biological fertilizer, rich in Bio-logical Value. It can undergo compaction and bio drying to have organic fertilizer in powder/granular form. The liquid fertilizer can also be prepared.
  Liquid/slurry/Pulp from BTP I & II: Nutrients can be extracted separately in the liquid form from BTP I & BTP II. This liquid can be used as 'bulk liquid' or 'pre product' for many purposes, in many types of industries as follows: It can be used for production or extraction of nutrients, can be used in cosmetics production/industry, in essence production/industry, in production of soap like products/industry, in paper and pulp industry, in dye industry, in some industries to treat their hazardous effluents/intermediate or end products, in preparation of laboratory medias, broths/industry, in pharmaceutical industry, as any type of animal feed, as cattle feed, biofertilizers/industry & in many other industries. Thus the liquid produced during processes of BTP I & II have high commercial value.

Sub-Plants based on either single or combined basis of BTP I, BTP II, & BTP III can be installed for various isolated purposes. They are as follows
  The entire BTP can sub-divided into some of the following sub-plants:
  I. Animal Feed Plant
    The prepared sludge; can be mixed with hay, or any similar product, bio-dried, compacted & can be used as cattle & other animal feeds
    The BW from vegetable market or any green BW can be used for preparing herbivorous animal feed.
    The BW from slaughter houses can be used for carnivorous & omnivorous animal feed or pedigree production.
  II. The BW from flower market & vegetable market can be used for essence, cosmetic & pharma products & so on.
  III. Use of Bulk liquid; Nutrients can be extracted separately in a liquid form from the BTP I & II. This liquid can be used as 'bulk liquid' or 'pre product' for many purposes & in many types of industries.
  IV. Use of materials used in BTP I, II: The 'Fluid' similar to ruminal fluid, which is used in the tank, contains various types, species of microbes. Controlled action/s of specific microbes on prepared sludge in the BTP I can be conducted to obtain a sludge of specific characteristic, which we can call as 'bulk liquid', which will be useful in many types of industries.
  V. Fertilizer plant—The end product of the complete process & from the BTP II is the fertilizer/biomass rich in Bio-logical Value. It can undergo compaction and bio drying to have organic fertilizer in powder/granular form. The liquid fertilizer can also be prepared. In a country like India the silt content deposited on the river basins & dams every year is very large in quantities. If this bio-fertilizer is mixed with the collected silt & if spread over any barren land of around 1 mt thickness, then that barren land will be converted into fertile land for hundreds of years.

Advantages of BTP are as follows
  I. Advantages of the Process
    The BTP can be called as the Pioneer of the "use of Natural Processes, with the help of Natural Materials, and mechanical procedures to enhance the process, by completely treating biodegradable waste (BW), to simple End products, easily acceptable to nature, in a very short span of time of 48 to 72 hrs. this time is very less as compared to existing process of land fill or composting
    The materials used for these natural processes, their independent or combined actions are used in BTP. All the materials are easily available in the market & are non hazardous.
    The total process is a chain of Easy to operate techniques & technologies, and the total process once established will run on its own even 24 hours per day and will require minimum man power, minimum supervision and minimum maintenance cost.
    The processes are occurring either in series or singly, since the entire plant is modular in nature it can have various capacities depending upon the requirement. The various stages, independently or combined, can also be carried out at different locations providing highest flexibility of operations.
  II. Advantages of materials of BTP I& II, by making variations in it or controlled actions of it:
    The 'Fluid' similar to ruminal fluid, which is used in the BTP I, (containing various types, species of microbes) & the 'Enzymes' used in BTP II are the materials. And as per requirement, controlled action/s of specific microbes or enzymes, on prepared sludge, can be conducted to obtain a sludge of specific characteristics, which can be called as 'bulk liquid', which will be useful as:
    As the substrate for various laboratory culture medias/its industry/suitable in various chemical Labs/Research Labs/Industrial Units for effluent treatment.
    The bulk liquid will be highly useful for various products & their relative industries like cosmetic products, soap related products, essence related products, paper & pulp like products/industry etc.

The bulk liquid can be useful for medicine production in the pharmaceutical Industry.

The bulk liquid can be used in nutritional products like protein powder, vitamins etc., after strict sterile treatments.

III. Advantages of Methane: The total process is anaerobic. Since it is conducted in closed silo which collects the entire gas generated from the process. Exact volumetric analysis of the effluent gas can be obtained.

The amount of Methane produced in the process can be collected & measured exactly. It can be burnt and finally the generated heat can be used either to run the plant or to generate electricity, thus to make the plant self sustainable. By advanced treatments it can be used as liquid gas or fuel, in future.

Methane is a potent green house gas contributing to Global Warming. As the methane is collected in closed container, it's release in the atmosphere and thus ultimately intensity of the global warming can be reduced. Municipal Authorities can obtain Carbon Credit of the same as an additional Revenue Income.

IV. Advantages from Financial Aspect of Modular Structure & Various Permutations for Installation.

The plants of small sizes (1 MT, 3 MT or 5 MT) can be worked out at a very low cost. Even for the plants with less capacity the suitable variation in the design of tank can be done. (e.g. a single tank can be prepared with different compartments with the help of baffle walls and the different materials of BTP I, II, III can be added to these compartments to get the same reactions & end products for a small scale plant)

Plants in various modules & of various capacities can be worked out (such as 25 MT/50 MT/75 MT/100 MT).

Thus, addition of module as per the requirement is possible, since the entire plant can be worked out in stages and the financial burden can be divided into stages.

The processes can be used at varied locations, as a whole or in modules, for different purposes & in varied capacities, providing flexibility.

The entire plant can be worked out in stages, i.e., the Stage—I activity can be worked out in very less area at various locations within the city or out side the city, which will considerably save the transportation cost of local governance. Even extracted water can be treated on the collection centre and the purified water can be used for street cleaning, watering for plantation along the roads or for civil gardens etc and prepared sludge should be transported to the main BTP site in the city.

The land area required is considerably less even for a large plant so the cost of acquisition of land is less.

Cost of installation of plant is very less as compared to other plants existing as on today. Less operation and maintenance cost since all the material are easily available.

This is a continuous process and the total plant can be set in such a way that it runs automatically and needs very less no of employees and thus ultimately will have a low administrative cost The total heat required can be generated from the burning of methane making the plant self sustainable & it can also provide an additional income to the local authorities by way of carbon credit Every by-product at every stage has commercial value V. Ecological Advantages The process of BTP is first of its kind, which completes the entire Ecological Cycle of Bio-mass within the specified period of 48-72 hours, when treated in BTP. This is not possible by any of the current methods applied for waste treatment such as composting or natural anaerobic digestion The liquid or powder fertilizer has a high biological value & when mixed with the soil, the soil bacteria use the organic matter of it, convert it into simple Nutrients which are easily accepted by the Plant from the soil and the entire Bio-mass Cycle will be completed.

Today the human population is increasing in logarithmic proportions and we are extracting huge amount of forests for fossil fuel, plants/vegetables, as our food for our day to day consumption. But it is not replaced by us in any natural form. To return the biomass to the nature we need to complete the cycle of Bio mass on a daily basis. For which we need to follow the law of daily processing i.e., the amount of nutrients extracted from nature (plants/vegetables) daily, has to be balanced or returned back to nature in the form of Nutrients (e.g. Ammonia, Urea, Nitrate) on a daily basis and BTP is the only process which will be able to satisfy the speed of extraction of nutrients from the nature.

In the BTP, every biological reaction is taking place in a natural sequence and by natural ways; there is no letchate formation in the entire process or liberation of Hazardous gases or methane causing air pollution.

The release of methane in the atmosphere from landfills is reduced due to proper treatment of BW & collection of methane into closed container. Methane is a potent green house gas, which by absorption of solar infrared radiation contributes to global warming. The intentisity of which is reduced due to BTP indirectly. If the BW is properly treated as in BTP it has a potential to reduce the temperature of the earth by min 0.25° C. in the $21^{st}$ Century.

Wastage of Land is avoided. land which is used for the open landfills cannot be used for at least the next 80 to 100 years.

VI. Advantages of Sub plants are as mentioned above.

Comparison Chart Between Existing Systems & BTP

The majority of existing systems, for the treatment of mixed MSW, are Land fill or incineration or mechanical biological treatment plants. Following is the comparison chart for all of them:

|  | Land fill | Incineration | MBT | BTP |
| --- | --- | --- | --- | --- |
| Location | Has to be at one end of the city | Has to be at one end of the city | Has to be at one end of the city | Since it is modular can be Installed in various modules at various locations |
| Transportation Cost to local Governance | Very high | Very high | Very high | Very low |
| Manual/mechanical Separation | Low | Low | Medium | Very high, since treating the waste depending upon the characteristics is the basic principle of plant. |
| Letache formation | Very high | Nil | Nil | Nil |

-continued

|  | Land fill | Incineration | MBT | BTP |
|---|---|---|---|---|
| Emission of hazardous gases | Very high | High | Medium | Nil |
| Loss of fertility of soil or water in nearby area | Very high | Dumping of Fly ash is major problem | Dumping of Fly is a major problem | Nil |
| Loss of Land | Permanent | Same plant on same location can be used for years together | Same plant on same location be used for years together | Same plant on same location can be used for years together |
| Health wise suitability for adjoining area | Dangerous | Dangerous | Dangerous | Helpful |
| Commercial usefulness/useful by products | Nil | Nil, instead Disposal of ash produced is a problem | Commercially useful to some extent | Commercially beneficial & has useful by products |
| Investment cost | High in the form land | Very high | High | Medium |
| Time required for process | Very long, even years | Short | Medium | Short |
| The potent GHG emission treatment | Not possible | Possible | Possible | Possible |
| Contribution in global warming | Very High | High | High | Lowest |
| Ecologically helpful | Not at all | To some extent | To some extent | Completely |
| Recycling of Biodegradable material | Hardly 30% of the nutrients may be going back to the ecological cycle or bio-mass cycle of the nature | Working exactly in the reverse way to ecological cycle | working Exactly in the reverse way to ecological cycle | 100% follows the ecological cycle or the bio-mass cycle |

Plant Design Calculations: for the Biological Treatment Plant (BTP)

1.1. The Biological treatment plant, BTP, can be designed in various sizes depending upon the various capacities as per requirement and generally, the plant can be made available in the following sizes.

| Plant Size | Suitable for |
|---|---|
| Mini plant in the Modules of 1 MT, 3 MT, 5 MT | For Small/medium residential colonies/Medium scale Commercial establishments/Educational Institutes/multiplexes etc. |
| Medium module of 10 MT 25 MT/50 MT 75 MT/100 MT | Large scale Commercial Establishments, For the Small/medium scale cities i.e., Taluka places Required to cover a dense population basin or a sector of a city |

1.2 Basic Volumetric Calculations of the Plant Considering Substrate Waste as MSW This entire process strictly works on the basis of segregation of mixed MSW, on the basis of the characteristics of the MSW. Also the preparation of clear sludge which is the main requirement of the processes of the plant.

When 1 MT of mixed MSW is collected on the BTP site, after manual separation of the collected waste 0.2 MT of MSW is of recyclable inorganic nature and can be separated out manually.

The remaining 0.8 MT of MSW, is conveyed to the Storage Tank

After the process of the Stage I i.e Preparation of Sludge in the primary treatment tank, the quantity of the remaining clear MSW is approximately 60% of 0.8 MT i.e. approx 0.5 MT.

Thus the actual prepared sludge available for the BTP will be to the tune of 0.5 MT and so on. But the plant capacity will be known for its total collected MSW thus for a 50 MT collection centre the actual prepared sludge will be to the tune of 25 MT, but the plant will be known as a 50 MT per day plant.

1.3 Sample Calculation of a 25 MT/Day Plant:—

I. Collection
  Collected MSW 25 MT=25,000 kg
II. Manual Separation
  After manual separation the recyclable MSW will be transported to the respective plants and the Balance quantity will be 80% of (1) 20 MT=20,000 kg
III. Primary Treatment Tank
  After the Stage I of Preparation of the Sludge 12 MT=12,000 kg
  The quantity of clear sludge will be 60% of (2)
  Thus the quantity of prepared sludge to undergo The series of processes in the BTP will be half since in 24 hours time we can have two Rotations of the tank of 12 hours each i.e. we can deliver the prepared sludge @ 500 kg per hour in, BTP I, Tank No-I and accordingly we will have to design the speed of pulley for the same 6 MT=6,000 kg
IV. Biological Treatment Plant I, Tank I (BTP I, Tank I)
  1. The intake of BTP I, TANK I is set for 1 MT/hr i.e. 1000 kg per hour then in the six hours the total intake in the tank will be of 6 MT which will have its own volume in the following manner.
  2. As per standards the volume of 1 CUM of mixed MSW carries a weight of 250 kg but after manual separation and after the treatment of the Stage I in primary treatment tank, 1 CUM of volume will have a weight of 500 kg and thus a prepared sludge of 6000 kg will have a volume of 12 CUM.
  3. In the BTP I, TANK I, addition of water along with microbes has to be done (to have the salival effect as in cow). Since the quantity of prepared sludge is known to us on Weight basis we can add 'Fluid', similar to cow's ruminal fluid on volumetric basis so as to have maximum utilization of Fluid & thus highest efficiency. (So the capacity required for addition of water will be 90 Ltr and 90 Lit of ruminal fluid for 30 kg of intake are the standard calculation in the digestive system of cow). So for the intake of 6000 kg we will require 36000 ltr or 36 cum of water.
4. Thus the total volumetric requirement of BTP I, TANK I, i.e. (2+3)=12+36=48 CUM
5. Tank size suggested—Squarish/Circular
6. Tank size provided—7.5 M×4.50 M×2=67.5 CUM
7. Volume provided is more than volume required
8. The said tank will have 12 hours of process time. (the microbes require only 13 minutes to multiply, but protozoa require 12 hours to 15 hours to multiply, so the sludge will be there in BTP TANK I for 12 hours thus the time duration will be 12 hours).

V. Intermediate Path
1. After 12 hours this volumetric sludge will be passed to the BTP II, TANK II. Prior to this, the sludge is passed through an intermediate path with acidic PH of approx. 2-2.5, so that the life of microbes will come to an end. the PH is made acidic by appropriate material (can be added in the form of concentrate) added on volumetric basis.
2. The previously lowered PH is to be raised towards the Alkaline side (approx. 7-7.2), by adding the appropriate material, on volumetric basis
3. The time required for the process is very short
4. Volume is not majorly altered VI. Biological Treatment Plant Tank II (BTP Tank II)
1. In the BTP II TANK II when the intake of 48 CUM is in process we have enzymatic action on calculated sludge since Enzymes can be sprinkled on this activated sludge to have maximum utilization and highest efficiency of BTP II, TANK II.
2. Since in the activated sludge the percentage of water is on higher side so addition of Enzymes in the form of Concentrates is also possible, so for the BTP TANK II additional provision is not made, The tank size is kept the same as BTPI, TANK I which will be sufficient.
3. The time required for the process is 12 hrs VII. Anaerobic Digestor BTP Tank III
1. The processed sludge will enter from BTP II, TANK III, into BTP III, TANK III, for Anaerobic Digestion. As the sludge will be entering from all the Tanks it is imagined that to complete the anaerobic digestion in BTP III the required time is 24 to 48 hrs. So this tank has been designed on the basis of three times the required volume of BTP II. After 72 hours the first set of volume will get discharged in form of liquid fertilizer and new set of volume from BTP II, Tank II will be added to Tank III. So minimum required volume of BTP TANK III=3×volume of BTP TANK II=3×48 CUM=144 CUM.
2. In BTP III, TANK III, there is no addition on volumetric basis from outside. To enhance the process only the Thermophilic Bacteria are added in the same sludge and controlled temperature and specific PH are maintained. So no additional volume is required than BTP III, TANK III.
3. From this tank sludge in the solid or liquid form is the out flow. The Process of methanogenesis of anaerobic digestion is bit slow, so instead of 24 hrs, provision has to made for 48 hrs. In that case Tank size required is 2 times that of above=2×144=288 CUM.
4. Volume provided for BTP III, TANK III=12 m×12 m×2 m=288 CUM.
5. Volume provided is more than the volume required.

VIII. Fertilizer Treatment
The effluent from BTP III, TANK III (if needed it can also be extracted from BTP Tank II) is in liquid form or in solid form. The liquid fertilizer will undergo some refinement procedure and after packed in bulk size container will be available for dispatched. If needed the processed sludge which is in semi solid condition and will undergo compaction and dehydration process and ultimately the powder form of the fertilizer will be available for dispatch.

IX. The Primary Treatment Tank in Stage I-A
1. In the primary Treatment Tank—we have approximately 6000 Kg or 6 MT prepared sludge i.e. its volume will be—24 CUM (i.e. 250 kg/CUM).
2. The volume of water under controlled temperature which will be required for addition is considered as double the size i.e. 2×24=48 CUM.
3. The required volume of the primary Treatment Tank=72 CUM i.e., 24 CUM+48 CUM.
4. Volume provided=22/7×d×d×¼=22/7×12×12×¼=113.14 CUM
5. The volume provided is more than the volume required X. Water Treatment Tank
1. The volumetric requirement of Extracted water Tank. T1 will be 48 CUM
2. In the Water Treatment Tank T1 i.e. in the extracted water the upper layer of oil and Grease will be removed and will undergo separate process and the remaining water will undergo the aerobic bacterial process, the aeration process and the chlorination process.
3. In the entire process of treatment of contaminated water, following path is followed;
a) Aerobic bacteria treatment
b) Aeration process
c) Chlorination process
4. Thus, any of the treatments do not involve any addition of materials from the outside. So the volume of water treatment tank T2 and T3 can be the same as required by T1
5. Volume provided in Tank T1=5.00×6.00×2=60.00 CUM. Same volume will continue for Tank 2 and Tank 3. So for water Treatment Plant always volume provided is more.

1.4 Time Flow Diagram for the Entire Plant (BTP):—
Time Chart or Bar Chart of the entire process in Biological Treatment Plant can be divided into two parts. Since this entire process can be easily divided into 2 stages i.e.
III) Stage I—The process of preparation of sludge—approx 24 hours
IV) Stage II—Biological Treatment processes on the prepared sludge
BTP-I—12 Hours
BTP-II—12 Hours
BTP-III—24 to 48 Hours
Total—72 Hours
Thus if Stage I and Stage II activities are in series on the same site, the ultimate end product will be available in 72 hours and if the stage I activity is taking place at collection centre then the ultimate end product can be made available in 48 hours. Thus the entire process can be completed in 24 hours and once this entire cycle is set, then the entire biodegradable waste collected from the collection point of the city can be converted into natural biological fertilizer in 72 hours. Since it is a continuous process another set of prepared sludge can be added everyday and the same quantity of fertilizer can be obtained every day and so on.

Example

Green House Gases Methane, CO2 & Biodegradable Waste (BW)

World population (WP)=600 c=60000 lac
BW=500 gm/person/day as an average
Total BW of world=WP*BW per capita=30000 lac kg/day=30 lac Metric ton (MT)/day
1000 kg (1MT) of BW produces=15000 lit (15 Metri Lit) of CH4
1 MT of BW=15 Ml CH4/day $$\begin{aligned} \text{world } CH4 \text{ emission} &= \text{world } BW * CH4/ML/D \\ &= 30 \; lac \; MT * 15 \\ &= 450 \; lac \; Metri \; Lit/D \\ &= 4500 \; gigalit/D \end{aligned}$$

World CO2 Emission=4500*20=9000 gigalit/Day
=The CO2 available to be utilized as a Carbon sink/for Carbon fixation/day, which can be obtained from the proper treatment of BW as, done in BTP The foregoing objects of the invention are accomplished and the problems and shortcomings associated with prior art techniques and approaches are overcome by the present invention described in the present embodiment.

Detailed descriptions of the preferred embodiment are provided herein; however, it is to be understood that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure, or matter The embodiments of the invention as described above and the methods disclosed herein will suggest further modification and alterations to those skilled in the art. Such further modifications and alterations may be made without departing from the spirit and scope of the invention.

I claim:

1. A method for biological treatment of biodegradable waste, the method comprising the steps of:
    loading mixed solid waste on a conveyor belt;
    passing the conveyor belt containing the mixed solid waste through a magnet chamber for separating metal parts from the mixed solid waste;
    passing the conveyor belt containing mixed solid waste through at least one separator, wherein biodegradable waste is separated from recyclable inorganic waste of mixed solid waste;
    collecting the separated biodegradable waste in a first storage tank;
    passing the separated biodegradable waste from the first storage tank to a primary treatment tank;
    treating the biodegradable waste in the primary treatment tank, wherein the treating in the primary treatment tank comprises mixing the biodegradable waste with hot water having temperature ranging from 70° C. to 140° C. to kill pathogens and simultaneously rotating the mixture with a rotor, then allowing natural settling, and repeating this treatment step at least twice for separating supernatant that contains non-degradable material from the naturally settled material, to form prepared sludge;
    dehydrating and compacting the prepared sludge;
    grinding and chopping the prepared sludge in a second storage tank to increase the surface area thereof;
    storing the prepared sludge in a third storage tank at a temperature ranging from 30° C. to 60° C.;
    treating the prepared sludge in a Biological Treatment Plant-I, wherein the prepared sludge is treated with a fluid comprising microbes, under anaerobic conditions, temperature ranging from 35° C. to 40° C., and pH of about pH 5.5 to pH 6.5, to form a treated slurry;
    treating the treated slurry in a Biological Treatment Plant-II, wherein the treated slurry is treated with enzymes, under anaerobic conditions, temperature ranging from 35° C. to 40° C., and pH of about pH 7.1 to pH 8.2; and
    treating the treated slurry in a Biological Treatment Plant-III, wherein the treated slurry is treated with thermophilic bacteria under anaerobic conditions at temperature ranging from 35° C. to 40° C.

2. The method of claim 1, wherein the fluid treatment in Biological Treatment Plant-I is used to digest carbohydrates, proteins and lipids.

3. The method of claim 1, further comprising the step of treating the separated supernatant from the primary treatment tank in a water treatment plant.

4. The method of claim 1, wherein methane gas is generated from Biological Treatment Plant-I and Biological Treatment Plant-III and the methane gas is collected in at least one gas collector.

5. The method of claim 1, wherein the fluid used in Biological Treatment Plant-I is ruminal fluid or is fluid that contains microbes found in ruminal fluid.

6. The method of claim 5, further comprising the step of separating at least a portion of the treated slurry from Biological Treatment Plant-I as enriched biomass for use in industrial application or for use in combination with the products of Biological Treatment Plant-II and Biological Treatment Plant-III.

7. The method of claim 1, further comprising the step of exposing the treated slurry from Biological Treatment Plant-I to oxygen or acidic pH to inactivate the microbes.

8. The method of claim 1, wherein the enzymes of the Biological Treatment Plant-II are enzymes found in the human digestive system.

9. The method of claim 8, further comprising the step of separating at least a portion of the enzyme-treated treated slurry from Biological Treatment Plant-II for use in industrial application or for use in combination with the products of Biological Treatment Plant-I and Biological Treatment Plant-III.

10. The method of claim 1, wherein the treating of the biodegradable waste in the primary treatment tank is conducted for approximately 24 hours; the treating in the Biological Treatment Plant-I is conducted for approximately 12 hours; the treating in the Biological Treatment Plant-II is conducted for approximately 12 hours; and the treating in the Biological Treatment Plant-III is conducted for approximately 24 to 48 hours.

11. The method of claim 1, wherein the method converts biodegradable waste into biological fertilizer.

12. The method of claim 11, further comprising the step of using the biological fertilizer.

* * * * *